(12) United States Patent
Arzel et al.

(10) Patent No.: US 7,772,256 B2
(45) Date of Patent: Aug. 10, 2010

(54) 2-HETEROARYL SUBSTITUTED BENZOTHIOPHENES AND BENZOFURANES 709

(75) Inventors: Erwan Arzel, Sodertalje (SE); Britt-Marie Swahn, Sodertalje (SE); David Wensbo, Lund (SE)

(73) Assignee: Astrazeneca AB, Sodertalje (SE)

( * ) Notice: Subject to any disclaimer, the term of this patent is extended or adjusted under 35 U.S.C. 154(b) by 191 days.

(21) Appl. No.: 12/042,795

(22) Filed: Mar. 5, 2008

(65) Prior Publication Data

US 2008/0221149 A1 Sep. 11, 2008

Related U.S. Application Data

(60) Provisional application No. 60/893,149, filed on Mar. 6, 2007.

(51) Int. Cl.
*A61K 31/443* (2006.01)
*C07D 405/04* (2006.01)

(52) U.S. Cl. .................... 514/337; 546/284.1
(58) Field of Classification Search .............. 546/284.1; 514/337
See application file for complete search history.

(56) References Cited

U.S. PATENT DOCUMENTS

| | | | |
|---|---|---|---|
| 4,232,010 A | 11/1980 | Tsukamoto et al. |
| 5,236,619 A | 8/1993 | Iwaki et al. |
| 5,518,713 A | 5/1996 | Raspanti |
| 2005/0101647 A1 | 5/2005 | Oda et al. |
| 2007/0258887 A1 | 11/2007 | Tamagnan et al. |
| 2008/0027051 A1 | 1/2008 | Malmstrom et al. |

FOREIGN PATENT DOCUMENTS

| | | |
|---|---|---|
| EP | 120589 B1 | 6/1988 |
| EP | 1612204 A1 | 1/2006 |
| JP | 2004250411 A | 9/2004 |
| JP | 11116476 A | 5/2008 |
| WO | 9517095 A1 | 6/1995 |
| WO | 0216333 A2 | 2/2002 |
| WO | 02051821 A1 | 7/2002 |
| WO | 02085903 A2 | 10/2002 |
| WO | 02092086 A1 | 11/2002 |
| WO | 03051859 A1 | 6/2003 |
| WO | 03106439 A1 | 12/2003 |
| WO | 2004008319 A2 | 1/2004 |
| WO | 2004012736 A1 | 2/2004 |
| WO | 2004083195 A1 | 9/2004 |
| WO | 2004101558 A1 | 11/2004 |
| WO | 2006030032 A1 | 3/2006 |
| WO | 2006125324 A1 | 11/2006 |
| WO | 2007033080 A2 | 3/2007 |
| WO | 2007035405 A2 | 3/2007 |
| WO | 2007047204 A1 | 4/2007 |
| WO | 2007063946 A1 | 6/2007 |
| WO | 2007086800 A1 | 8/2007 |
| WO | 2007149030 A1 | 12/2007 |
| WO | 2008091195 A1 | 7/2008 |

OTHER PUBLICATIONS

Allsop et al., "3-p-Toluoyl-2-[4'-(3-diethylaminopropoxy)-phenyl]-benzofuran and 2-[4'-(3-diethylaminopropoxy)-phenyl]-benzofuran Do Not Act as Surfactants or Micelles when Inhibiting the Aggregation of β-Amyloid Peptide", Bioorg. Med.Chem.Lett, 2001, 255-257, 11(2).
Barni, et al., "2-(Methylpyridyl or quinoly)benz-X-azoles, Salts and Polymethine Dyes (1)", Journal of Heterocyclic Chemistry, 1979, P1579-82, 16(8).
Cai et al., "Synthesis an Evaluation of Two 18F—Labeled 6-Iodo (4-N,N-dimethylamino)phenylimidazo [1,2-a] pyridine Derivatives as Prospective Radioligands for β-Amyloid in Alzheimer's Disease", J.Med.Chem, 2004, 2208-2218, 47 (9).
Chang et al., "Synthesis and evalution of benzothiophene derivatives as ligands for imagining β-amyloid plaques in Alzheimer's disease", Nuclear Medicine and Biology, 2006, 811-820, 33.
Choi at al., "Synthesis of 2-(4-Hydroxyphenyl)benzofurans and Their Application to b-Amyloid Aggregation Inhibitor", Archives of Pharmacal Research, 2004, 19-24, 27(1).
Coimbra et al., "The Role of MRI and PET/SPECT in Alzheimer's Disease", Curr.Top.Med.Chem, 2006, 629-647, vol. 6.

(Continued)

*Primary Examiner*—Kamal A Saeed
*Assistant Examiner*—Samantha L Shterengarts
(74) *Attorney, Agent, or Firm*—John A. Cleveland, Jr.

(57) ABSTRACT

The present invention relates to novel 2-heteroaryl substituted benzothiophene and benzofuran derivatives, precursors thereof, and therapeutic uses of such compounds, having the structural formula (Ia) below:

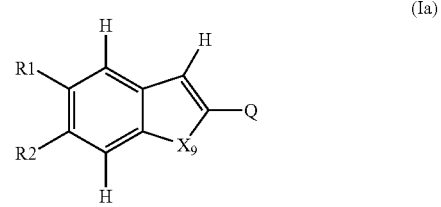

(Ia)

and to their pharmaceutically acceptable salt, compositions and methods of use. Furthermore, the invention relates to novel 2-heteroaryl substituted benzothiophene and benzofuran derivatives that are suitable for imaging amyloid deposits in living patients, their compositions, methods of use and processes to make such compounds. More specifically, the present invention relates to a method of imaging amyloid deposits in brain in vivo to allow antemortem diagnosis of Alzheimer's disease as well as measuring clinical efficacy of Alzheimer's disease therapeutic agents.

6 Claims, No Drawings

OTHER PUBLICATIONS

Guram et al., "New Catalysts for Suzuki-Miyaura Coupling Reactions of Heteroactom-Substituted Heteroaryl Chlorides", J. Org. Chem. 2007, p. 5104-5112, vol. 72.

Hardy et al., "The Amyloid Hypothesis of Alzheimer's Disease: Progress and Problems on the Road to Therapeutics", J. Science, 2002, 353-356, 297.

Howlett et al., "Inhibition of fibril formation in β-amyloid peptide by a novel series of benzofurans", Biochemical Journal, 1999, 283-289, 340(1).

Klunk et al., "Imaging Brain Amyloid in Alzheimer's Disease with Pittsburg Compound-B", Ann Neurol, 2004, 306-319, 55.

Kung et al., "IMPY: an improved thioflavin-T derivative for in vivo labeling of β-amyloid plaques", Brain Research, 2002, 202-210, 956.

Kung et al., "Binding of two potential imaging agents targeting amyloid plaques in postmortem brain tissues of patients with Alzheimer's disease", Brain Research, 2004, 98-105, 1025(1-2).

Kung et al., Erratum to "Binding of two potential imaging agents targeting amyloid plaques in postmortem brain tissues of patients with Alzheimer's disease", Brain Research, 2005, 302, 1031 (2).

Lockhart et al., "Evidence of the Presence of Three Distint Binding Sites for the Thioflavin T Class of Alzheimer's Disease PET Imaging Agents on β-Amyloid Peptide Fibrils", J Biol.Chem., 2005, 7677-7684, 280(9).

Lu, et al., "Synthesis and biodistribution of [131I]IMPY", Nuclear Science and Techniques, 2005, 289-292, 16(5).

Mathis et al., "Synthesis and Evalution of 11C-Labeled 6-Substituted 2-Arylbenzothiazoles as Amyloid Imaging Agents", Med Chem., 2003, 2740-2754, 46.

Miller, "A Better View of Brain Disorders", Science, 2006, 1376, 313.

Newberg et al., Safety, Biodistribution, and Dosimetry of 123I-IMPY: A Novel Amyloid Plaque-Imaging Agent for the Diagnosis of Alzheimer's Disease, Journal of Nuclear Medicine, 2006, 748-754, 47(5).

Nordberg, A. "PET imaging of amyloid in Alzheimer's disease", Lancet, Neurol., 2004, 519-527, 3.

Ono et al., Benzofuran derivatives as Aβ-aggregate-specific imaging agents for Alzheimer's disease, Nuclear Med. Biol., 2002, 633-642, 29(6).

Ono et al., "Synthesis and biological evaluation of (E)-3-styrylpyridine derivatives as amyloid imaging agents for Alzheimer's disease", Nuclear Medicine and Biology, 2005, 329-335, 32.

Ono et al., "Novel Benzofuran Derivatives for PET Imaging of β-Amyloid Plaques in Alzheimer's Disease Brains", J. Med. Chem., 2006, 2725-2730, 49.

Shi et al., "Antitumor Benzothiazoles. 3.1 Synthesis of 2-(4-Aminophenyl) benzothiazoles and Evaluation of Their Activities against Breast Cancer Cell Lines in Vitro and in Vivo", Journal of Medicinal Chemistry, 1996, 3375-3384, 39 (17).

Shoghi-Jadid et al., "Localization of Neurofibrillary Tangles and Beta-Amyloid Plaques in the Brains of Living Patients With Alzheimer Disease",The American Journal of Geriatric Psychiatry, 2002, 24-35,10.

Thakak et al., "Reaction of guanidine with 3-formylchromones", Journal of the Indian Chemical Society, 1984, 550-2, 61(6): JICSAH;ISSN: 0019-4522.

Twyman et al., "A Short Synthesis of the β-amyloid (Aβ) Aggregation Inhibitor 3-p-Toluoyl-2-[4'-(3-diethylaminopropoxy)-phenyl]-benzofuran", Tetrahedron Lett, 1999, 9383-9384, 40(52).

Zeng et al., "Synthesis and evaluation of two 18F-labeled imidazol [1,2-a]pyridine analogues as potential agents for imaging β-amyloid in Alzheimer's disease", Bioorganic & Medicinal Chemistry Letters, 2006, 3015-3018, 16(11).

Zhang et al., "F-18 Stilbenes as PET Imaging Agents for Detecting β-Amyloid Plaques in the Brain", J.Med. Chem., 2005, 5980-5988, 48.

Zhang et al., "18F-labeled styrylpyridines as PET agents for amyloid plaque imaging", Nuclear Medicine and Biology, 2007, 89-97, 34.

Zhuang et al., "IBOX (2-(4'-dimethylaminophenyl)-6-iodobenzoxazole) : a ligand for imaging amyloid plaques in the brain", Nuclear Medicine and Biology, 2002, 887-894, 28(8), CODEN:NMBIEO;ISSN:0969-8051.

Zhuang et al., "Structure-Activity Relationship of Imidazo[1,2-a]pyridines as Ligands for Detecting β-Amyloid Plaques in the Brain", Journal of Medicinal Chemistry, 2003, 237-243, 46(2).

English abstract for JP11116476.

English abstract for JP2004250411.

STN International, File CAPLUS, CAPLUS accession No. 1988:580390, document No. 109:180390, Shiino, Yasuko et al., "Electrophotographic charge-generating disazo photoconductors", & JP, A, 63094248, 19880425.

STN International, File HCAPLUS, HCAPLUS accession No. 1999:476741, Document No. 131:228612, Benhida, Rachid et al:"Synthesis of 6-allyl—and 6-heteroarylindoles by palladium catalyzed stille cross-coupling reaction", &Tetrahedron Letters (1999), 40(31), 5701-5703.

158229 CAPLUS, AN 2002:293449, DN 136:319426.

STN International, File CAPLUS, CAPLUS accession No. 2003:60939, document No. 138:287190, Soares-Santos, P.C.R. et al., "Blue-emitting flurophores based on 1,3-benzoxazolyl and 1,3-benzothiazolyl-substituted indoles and carbazoles", & Advances in Colour Science and Technology (2002), 5(4), 94-98.

International Search Report for International Application No. PCT/SE2008/050243.

Swedish Patent Office Search Report dated Sep. 27, 2007.

Vippagunta et al., Crystalline Solids:, 2001, Advanced Drug Delivery Reviews, 48, pp. 3 and 18.

Office Action for U.S. Appl. No. 11/763,151 mailed Aug. 6, 2008.

Office Action for U.S. Appl. No. 11/763,151 mailed Jun. 12, 2008.

2-HETEROARYL SUBSTITUTED BENZOTHIOPHENES AND BENZOFURANES
709

This patent claims the benefit of priority to U.S. Provisional Patent Application No. 60/893,149 (filed Mar. 6, 2007). The entire text of U.S. Provisional Patent Application No. 60/893,149 is incorporated by reference into this patent.

The present invention relates to novel 2-heteroaryl substituted benzothiophene and benzofuran derivatives and therapeutic uses for such compounds. Furthermore, the invention relates to novel 2-heteroaryl substituted benzothiophene and benzofuran derivatives that are suitable for imaging amyloid deposits in living patients, their compositions, methods of use and processes to make such compounds. More specifically, the present invention relates to a method of imaging amyloid deposits in brain in vivo to allow antemortem diagnosis of Alzheimer's disease as well as measuring clinical efficacy of Alzheimer's disease therapeutic agents.

BACKGROUND OF THE INVENTION

Amyloidosis is a progressive, incurable metabolic disease of unknown cause characterized by abnormal deposits of protein in one or more organs or body systems. Amyloid proteins are manufactured, for example, by malfunctioning bone marrow. Amyloidosis, which occurs when accumulated amyloid deposits impair normal body function, can cause organ failure or death. It is a rare disease, occurring in about eight of every 1,000,000 people. It affects males and females equally and usually develops after the age of 40. At least 15 types of amyloidosis have been identified. Each one is associated with deposits of a different kind of protein.

The major forms of amyloidosis are primary systemic, secondary, and familial or hereditary amyloidosis. There is also another form of amyloidosis associated with Alzheimer's disease. Primary systemic amyloidosis usually develops between the ages of 50 and 60. With about 2,000 new cases diagnosed annually, primary systemic amyloidosis is the most common form of this disease in the United States. Also known as light-chain-related amyloidosis, it may also occur in association with multiple myeloma (bone marrow cancer). Secondary amyloidosis is a result of chronic infection or inflammatory disease. It is often associated with Familial Mediterranean fever (a bacterial infection characterized by chills, weakness, headache, and recurring fever), Granulomatous ileitis (inflammation of the small intestine), Hodgkin's disease, Leprosy, Osteomyelitis and Rheumatoid arthritis.

Familial or hereditary amyloidosis is the only inherited form of the disease. It occurs in members of most ethnic groups, and each family has a distinctive pattern of symptoms and organ involvement. Hereditary amyloidosis is though to be autosomal dominant, which means that only one copy of the defective gene is necessary to cause the disease. A child of a parent with familial amyloidosis has a 50-50 risk of developing the disease.

Amyloidosis can involve any organ or system in the body. The heart, kidneys, gastrointestinal system, and nervous system are affected most often. Other common sites of amyloid accumulation include the brain, joints, liver, spleen, pancreas, respiratory system, and skin.

Alzheimer's disease (AD) is the most common form of dementia, a neurologic disease characterized by loss of mental ability severe enough to interfere with normal activities of daily living, lasting at least six months, and not present from birth. AD usually occurs in old age, and is marked by a decline in cognitive functions such as remembering, reasoning, and planning.

Between two and four million Americans have AD; that number is expected to grow to as many as 14 million by the middle of the 21st century as the population as a whole ages. While a small number of people in their 40s and 50s develop the disease, AD predominantly affects the elderly. AD affects about 3% of all people between ages 65 and 74, about 20% of those between 75 and 84, and about 50% of those over 85. Slightly more women than men are affected with AD, even when considering women tend to live longer, and so there is a higher proportion of women in the most affected age groups.

The accumulation of amyloid Aβ-peptide in the brain is a pathological hallmark of all forms of AD. It is generally accepted that deposition of cerebral amyloid Aβ-peptide is the primary influence driving AD pathogenesis. (Hardy J and Selkoe D. J., Science. 297: 353-356, 2002).

Imaging techniques, such as positron emission tomography (PET) and single photon emission computed tomography (SPECT), are effective in monitoring the accumulation of amyloid deposits in the brain and correlating it to the progression of AD (Shoghi-Jadid et al. The American journal of geriatric psychiatry 2002, 10, 24; Miller, Science, 2006, 313, 1376; Coimbra et al. Curr. Top. Med. Chem. 2006, 6, 629; Nordberg, Lancet Neurol. 2004, 3, 519). The application of these techniques requires the development of radioligands that readily enter the brain and selectively bind to amyloid deposits in vivo.

A need exists for amyloid binding compounds that can cross the blood-brain barrier, and consequently, can be used in diagnostics. Furthermore, it is important to be able to monitor the efficacy of the treatment given to AD patients, by measuring the effect of said treatment by measuring changes of AD plaque level.

Properties of particular interest of a detectable amyloid-binding compound, besides high affinity for amyloid deposits in vivo and high and rapid brain entrance, include low unspecific binding to normal tissue and rapid clearance from the same. These properties are commonly dependant on the lipophilicity of the compound (Coimbra et al. Curr. Top. Med. Chem. 2006, 6, 629). Among the proposed small molecules for imaging amyloid plaques, some uncharged analogs of thioflavin T of potential use have been synthesized (Mathis et al. J. Med. Chem. 2003, 46, 2740). Different isosteric heterocycles are reported as potential amyloid binding ligands (Cai et al. J. Med. Chem. 2004, 47, 2208; Kung et al. J. Med. Chem. 2003, 46, 237). Benzofuran derivatives have previously been described for use as amyloid imaging agents (Ono et al. J. Med. Chem. 2006, 49, 2725; Lockhart et al. J. Biol. Chem. 2005, 280(9), 7677; Kung et al. Nuclear Med. Biol. 2002, 29(6), 633; WO2003051859 and for use in preventing Abeta aggregation (Twyman et al. Tetrahedron Lett. 1999, 40(52), 9383; Howlett et al. Biochemical Journal 1999, 340(1), 283; Choi et al. Archives of Pharmacal Research 2004, 27(1), 19; Twyman et al. Bioorg. Med. Chem. Lett. 2001, 11(2), 255; WO9517095).

Benzothiophene derivatives have previously been described for use as amyloid imaging agents (Chang et al. Nuclear Medicine and Biology 2006, 33, 811) and for use as neuroprotectant against β-amyloid toxicity (JP11116476). There is a need for improved compounds in order to obtain a signal-to-noise ratio high enough to allow detailed detection of amyloid deposits throughout all brain regions, and providing improved reliability in quantiative studies on amyloid plaque load in relation to drug treatments. The present invention provides novel 2-heteroaryl substituted benzothiophene and benzofuran derivatives for use as amyloid imaging agents and treatment of amyloid related diseases.

DISCLOSURE OF THE INVENTION

There is provided compounds of formula (Ia):

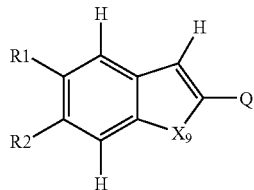

(Ia)

wherein
R1 is selected from H, halo, methyl, $C_{1-5}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, methoxy, $C_{1-5}$ fluoroalkoxy, $C_{1-5}$ alkylthio, $C_{1-5}$ fluoroalkylthio, amino, NH$C_{1-3}$ alkyl, NH$C_{1-3}$ fluoroalkyl, N($C_{1-3}$ alkyl)$_2$, N($C_{1-3}$ alkyl)$C_{1-3}$ fluoroalkyl, NH(CO)$C_{1-3}$ alkyl, NH(CO)$C_{1-3}$ fluoroalkyl, NH(CO)$C_{1-3}$ alkoxy, NH(CO)$C_{1-3}$ fluoroalkoxy, NHSO$_2C_{1-3}$ alkyl, NHSO$_2C_{1-3}$ fluoroalkyl, (CO)$C_{1-3}$ alkyl, (CO)$C_{1-3}$ fluoroalkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene), cyano, SO$_2$NH$C_{1-3}$ fluoroalkyl, nitro and SO$_2$NH$_2$;
R2 is selected from H, halo, methyl, $C_{1-5}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, methoxy, $C_{1-5}$ fluoroalkoxy, $C_{1-5}$ alkylthio, $C_{1-5}$ fluoroalkylthio, amino, NH$C_{1-3}$ alkyl, NH$C_{1-3}$ fluoroalkyl, N($C_{1-3}$ alkyl)$_2$, N($C_{1-3}$ alkyl)$C_{1-3}$ fluoroalkyl, NH(CO)$C_{1-3}$ alkyl, NH(CO)$C_{1-3}$ fluoroalkyl, NH(CO)$C_{1-3}$ alkoxy, NH(CO)$C_{1-3}$ fluoroalkoxy, NHSO$_2C_{1-3}$ alkyl, NHSO$_2C_{1-3}$ fluoroalkyl, (CO)$C_{1-3}$ alkyl, (CO)$C_{1-3}$ fluoroalkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene), cyano, SO$_2$NH$C_{1-3}$ fluoroalkyl, nitro and SO$_2$NH$_2$; or
R1 and R2 together forms a ring;

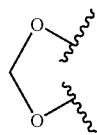

$X_9$ is selected from O and S.
Q is a nitrogen-containing aromatic heterocycle selected from Q1 to Q10;

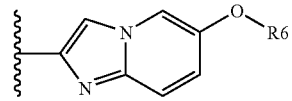 Q1

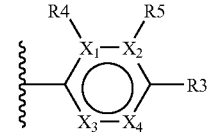 Q2

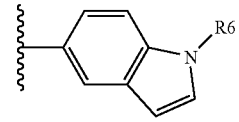 Q3

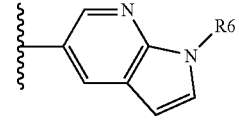 Q4

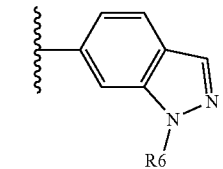 Q5

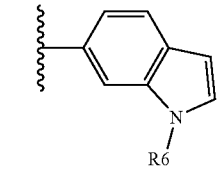 Q6

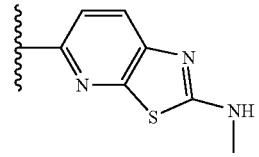 Q7

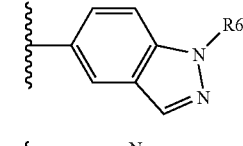 Q8

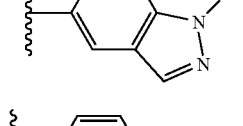 Q9

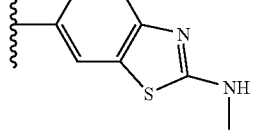 Q10 wherein
Q2 is a 6-membered aromatic heterocycle containing one or two N atoms, wherein $X_1$, $X_2$, $X_3$ and $X_4$ are independently selected from N or C; and wherein one or two of $X_1$, $X_2$, $X_3$ and $X_4$ is N and the remaining is C, and wherein the atom $X_1$ is C, said C is substituted with R4; and wherein the atom $X_2$ is C, said C is substituted with R5;

R3 is selected from methoxy, $C_{1-4}$ fluoroalkoxy, amino, $NHC_{1-3}$ alkyl, $NHC_{1-3}$ fluoroalkyl, $N(C_{1-3}$ alkyl$)_2$, $N(C_{1-3}$ alkyl$)C_{1-3}$ fluoroalkyl, $NH(CO)C_{1-3}$ alkyl, $NH(CO)C_{1-3}$ fluoroalkyl, NH(CO)G2, $(CO)NH_2$, $(CO)C_{1-3}$ alkoxy, methylthio, $C_{1-6}$ fluoroalkylthio, $SO_2NH_2$, $N(C_{4-6}$ alkylene) and G1;

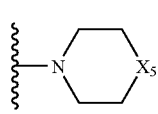

G1

$X_5$ is selected from O, NH, $NC_{1-3}$ alkyl and N(CO)Ot-butyl;

G2 is phenyl or a 5- or 6-membered aromatic heterocycle, optionally substituted with one substituent selected from fluoro, $C_{1-3}$ alkoxy, $C_{1-3}$ fluoroalkoxy and iodo;

R4 is selected from H and halo;

R5 is selected from H, fluoro, bromo and iodo;

R6 is selected from H, methyl and $(CH_2)_{0-4}CH_2F$;

one or more of the constituting atoms optionally is a detectable isotope;

as a free base or a pharmaceutically acceptable salt, solvate or solvate of a salt thereof;

with the provisio that the following compounds are excluded:

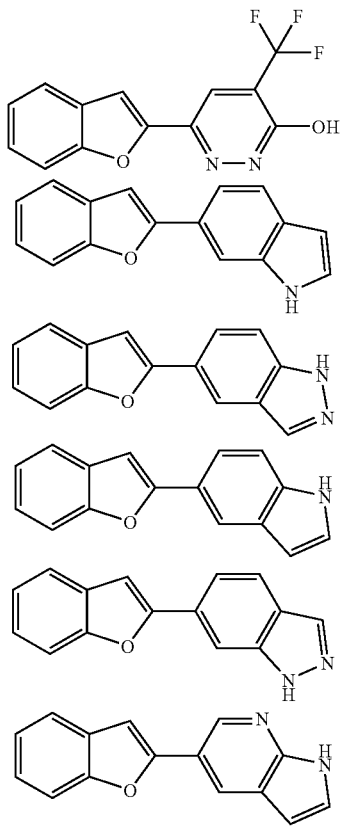

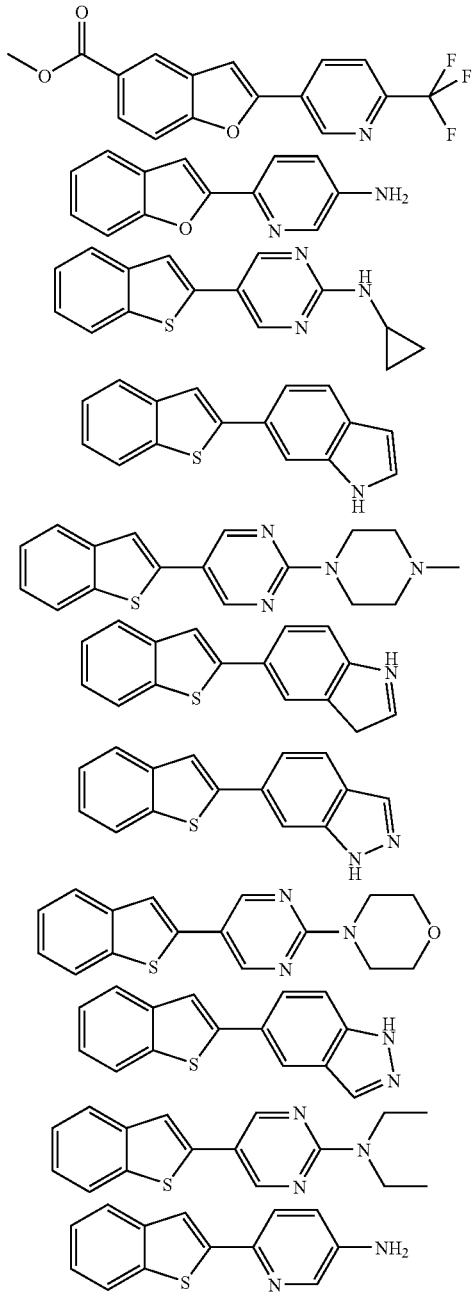

In one aspect there is provided compounds of formula (Ia), wherein R4 is selected from H, fluoro, bromo and iodo.

In another aspect there is provided compounds of formula (Ia), wherein R1 is selected from H, halo, methyl, $C_{1-5}$ fluoroalkyl, hydroxy, methoxy, $C_{1-5}$ fluoroalkoxy, methylthio, $C_{1-5}$ fluoroalkylthio, amino, NHmethyl, $NHC_{1-3}$ fluoroalkyl, $N(CH_3)CH_3$, $N(C_{1-3}$ alkyl$)C_{1-3}$ fluoroalkyl, $NH(CO)C_{1-3}$ alkyl, $NH(CO)C_{1-3}$ fluoroalkyl, $NH(CO)C_{1-3}$ alkoxy, $NH(CO)C_{1-3}$ fluoroalkoxy, $NHSO_2C_{1-3}$ alkyl, $NHSO_2C_{1-3}$ fluoroalkyl, $(CO)C_{1-3}$ fluoroalkyl, $(CO)C_{1-3}$ alkoxy, $(CO)C_{1-3}$ fluoroalkoxy, $(CO)NH_2$, $(CO)NHC_{1-3}$ fluoroalkyl, cyano, $SO_2NHC_{1-3}$ fluoroalkyl, nitro and $SO_2NH_2$; or R1 and R2 together forms a ring;

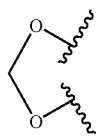

In another aspect there is provided compounds of formula (Ia), wherein R1 is selected from H, fluoro, iodo, methyl, $C_{1-5}$ fluoroalkyl, hydroxy, methoxy, cyano, $C_{1-5}$ fluoroalkoxy, methylthio, amino, NHmethyl, $NHC_{1-3}$ fluoroalkyl, NH(CO)$C_{1-3}$ alkyl, NH(CO)$C_{1-3}$ fluoroalkyl, NH(CO)$C_{1-3}$ fluoroalkoxy, (CO)$C_{1-3}$ alkoxy and (CO)$NH_2$.

In another aspect there is provided compounds of formula (Ia), wherein R1 is selected from H, hydroxy and methoxy.

In another aspect there is provided compounds of formula (Ia), wherein R2 is selected from H, fluoro, iodo, $C_{1-5}$ fluoroalkyl, hydroxy, methoxy, (CO)$NH_2$, cyano and methylthio.

In another aspect there is provided compounds of formula (Ia), wherein R2 is selected from H, fluoro, hydroxy and methoxy.

In another aspect there is provided compounds of formula (Ia), wherein R2 is H.

In another aspect there is provided compounds of formula (Ia), wherein Q is Q1.

In another aspect there is provided compounds of formula (Ia), wherein Q is Q2.

In another aspect there is provided compounds of formula (Ia), wherein Q is selected from Q3 to Q10.

In another aspect there is provided compounds of formula (Ia), wherein Q2 is a pyridine ring, wherein $X_3$ and $X_4$ are independently selected from N or C, and wherein one of $X_3$ and $X_4$ is N and the remaining of $X_1$, $X_2$, $X_3$ and $X_4$ are C.

In another aspect there is provided compounds of formula (Ia), wherein Q2 is a pyrimidine ring, wherein $X_2$ and $X_4$ are N, and wherein $X_1$ and $X_3$ are C.

In another aspect there is provided compounds of formula (Ia), wherein Q2 is a pyrimidine ring, wherein $X_1$ and $X_3$ are N, and wherein $X_2$ and $X_4$ are C.

In another aspect there is provided compounds of formula (Ia), wherein Q2 is a pyridazine ring, wherein $X_3$ and $X_4$ are N, and wherein $X_1$ and $X_2$ are C.

In another aspect there is provided compounds of formula (Ia), wherein Q2 is a pyrazine ring, wherein $X_1$ and $X_4$ are N, and wherein $X_2$ and $X_3$ are C; or wherein $X_1$ and $X_4$ are C, and wherein $X_2$ and $X_3$ are N.

In another aspect there is provided compounds of formula (Ia), wherein R3 is selected from methoxy, $C_{1-4}$ fluoroalkoxy, amino, $NHC_{1-3}$ alkyl, $NHC_{1-3}$ fluoroalkyl, $N(C_{1-3}$ alkyl$)_2$, $N(C_{1-3}$ alkyl$)C_{1-3}$ fluoroalkyl, NH(CO)$C_{1-3}$ alkyl, NH(CO)$C_{1-3}$ fluoroalkyl, (CO)$NH_2$, (CO)$C_{1-3}$ alkoxy, methylthio, $C_{1-6}$ fluoroalkylthio, $SO_2NH_2$, and G1; wherein $X_5$ is selected from O, NH and Nmethyl.

In another aspect there is provided compounds of formula (Ia), wherein R3 is selected from amino, NHmethyl and (CO)$NH_2$.

In another aspect there is provided compounds of formula (Ia), wherein R4 is selected from H and fluoro.

In another aspect there is provided compounds of formula (Ia), wherein R4 is H.

In another aspect there is provided compounds of formula (Ia), wherein R4 is fluoro.

In another aspect there is provided compounds of formula (Ia), wherein R5 is selected from H and fluoro.

In another aspect there is provided compounds of formula (Ia), wherein R5 is H.

In another aspect there is provided compounds of formula (Ia), wherein R5 is fluoro.

In another aspect there is provided compounds of formula (Ia), wherein R6 is selected from H and methyl.

In another aspect there is provided compounds of formula (Ia), wherein R6 is H.

In another aspect there is provided compounds of formula (Ia), wherein R6 is methyl.

In another aspect there is provided compounds of formula (Ia), said compound being:

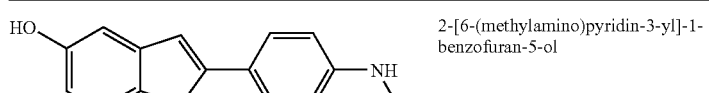

2-[6-(methylamino)pyridin-3-yl]-1-benzofuran-5-ol

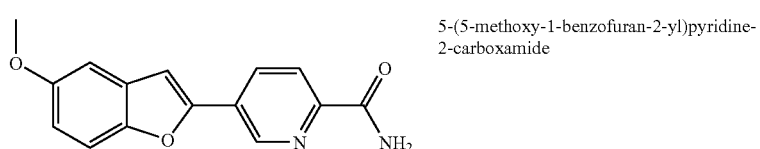

5-(5-methoxy-1-benzofuran-2-yl)pyridine-2-carboxamide

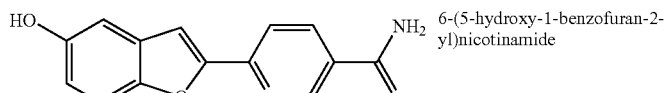

6-(5-hydroxy-1-benzofuran-2-yl)nicotinamide

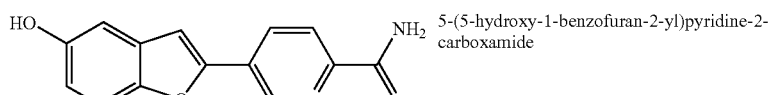

5-(5-hydroxy-1-benzofuran-2-yl)pyridine-2-carboxamide

-continued

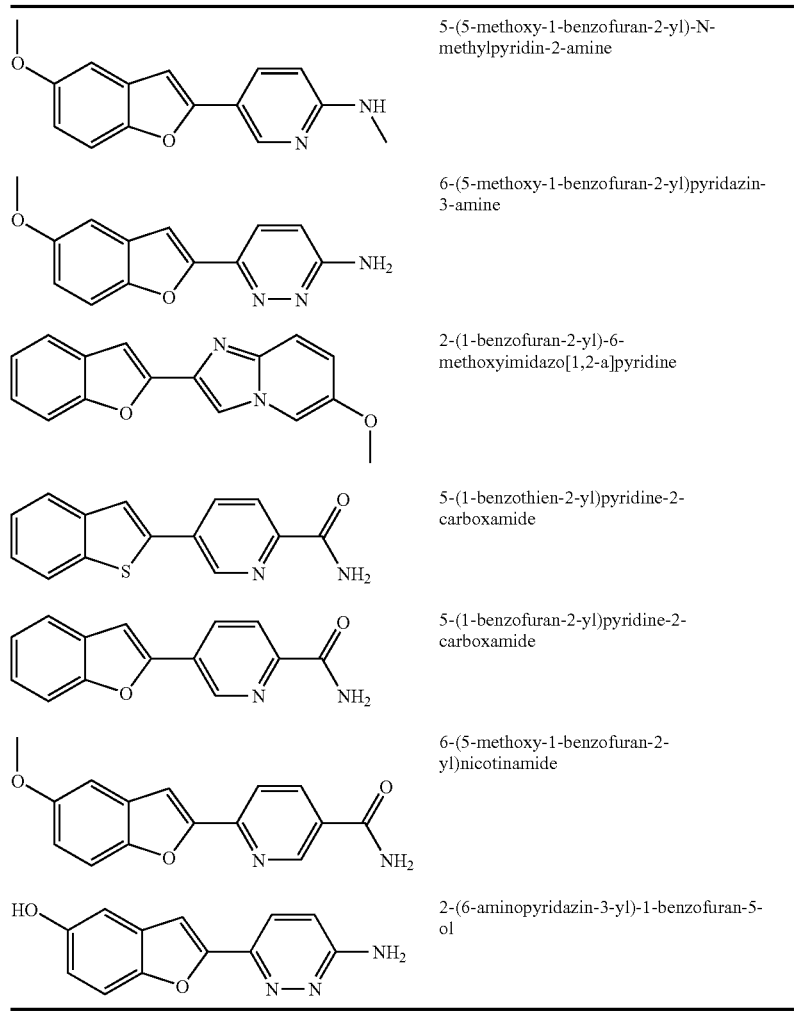

| | |
|---|---|
| | 5-(5-methoxy-1-benzofuran-2-yl)-N-methylpyridin-2-amine |
| | 6-(5-methoxy-1-benzofuran-2-yl)pyridazin-3-amine |
| | 2-(1-benzofuran-2-yl)-6-methoxyimidazo[1,2-a]pyridine |
| | 5-(1-benzothien-2-yl)pyridine-2-carboxamide |
| | 5-(1-benzofuran-2-yl)pyridine-2-carboxamide |
| | 6-(5-methoxy-1-benzofuran-2-yl)nicotinamide |
| | 2-(6-aminopyridazin-3-yl)-1-benzofuran-5-ol |

In another aspect there is provided compounds of formula (Ia), said compound being:

In another aspect there is provided a compound wherein one to six of the composing atoms is the detectable isotope

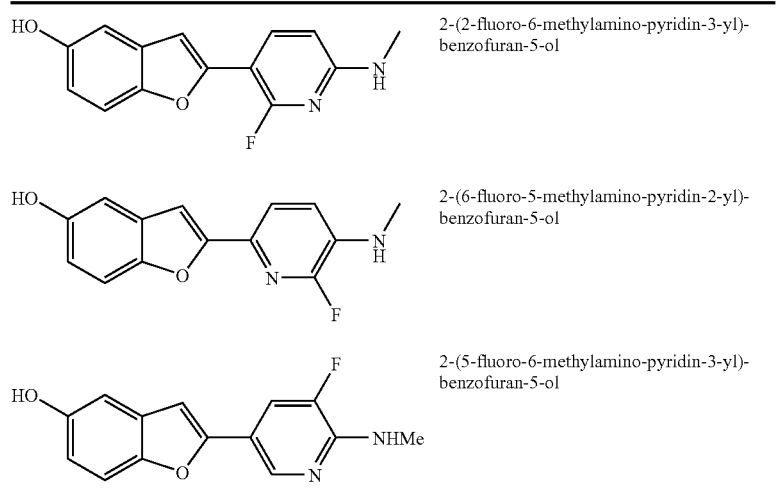

| | |
|---|---|
| | 2-(2-fluoro-6-methylamino-pyridin-3-yl)-benzofuran-5-ol |
| | 2-(6-fluoro-5-methylamino-pyridin-2-yl)-benzofuran-5-ol |
| | 2-(5-fluoro-6-methylamino-pyridin-3-yl)-benzofuran-5-ol |

$^3H$, or wherein one to three of the composing atoms is the detectable isotope $^{13}C$, or wherein one of the composing atoms is a detectable isotope selected from $^{18}F$, $^{11}C$, $^{75}Br$, $^{76}Br$, $^{120}I$, $^{123}I$, $^{125}I$, $^{131}I$ and $^{14}C$, said compound being selected from:

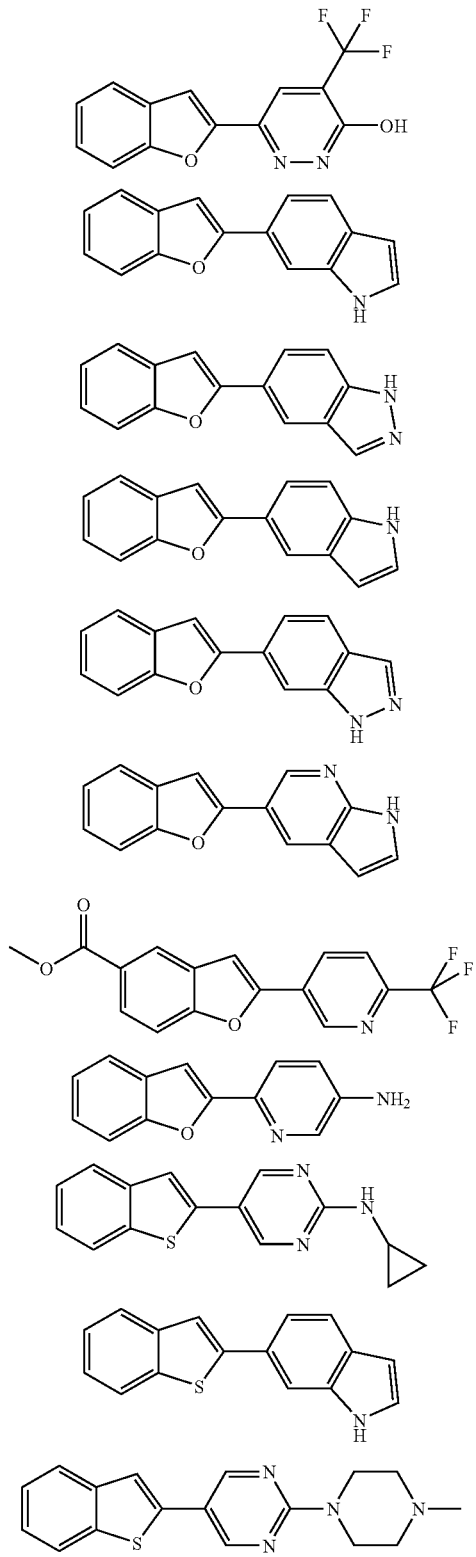

-continued

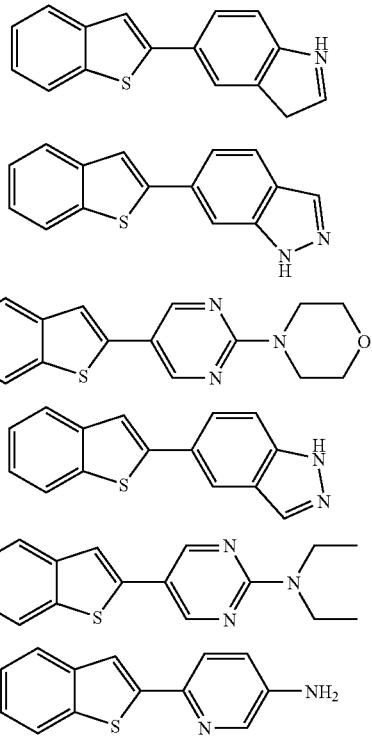

In one embodiment of this aspect, one of the composing atoms is the detectable isotope $^{11}C$. In another embodiment of this aspect, one of the composing atoms is the detectable isotope $^{18}F$.

In another aspect there is provided compounds of formula (Ia), wherein one or more of the atoms of the molecule represents a detectable isotope.

In another aspect there is provided compounds of formula (Ia), wherein one to six of the composing atoms is the detectable isotope $^3H$, or wherein one to three of the composing atoms is a detectable isotope selected from $^{19}F$ and $^{13}C$, or wherein one of the composing atoms is a detectable isotope selected from $^{18}F$, $^{11}C$, $^{75}Br$, $^{76}Br$, $^{120}I$, $^{123}I$, $^{125}I$, $^{131}I$ and $^{14}C$.

In another aspect there is provided compounds of formula (Ia), wherein one to six of the composing atoms is the detectable isotope $^3H$, or wherein one to three of the composing atoms is the detectable isotope $^{19}F$, or wherein one of the composing atoms is a detectable isotope selected from $^{18}F$, $^{11}C$ and $^{123}I$.

In another aspect there is provided compounds of formula (Ia), wherein one to six of the composing atoms is the detectable isotope $^3H$, or wherein one to three of the composing atoms is the detectable isotope $^{19}F$, or wherein one of the composing atoms is a detectable isotope selected from $^{18}F$ and $^{11}C$.

In another aspect there is provided compounds of formula (Ia), wherein one of the composing atoms is the detectable isotope $^{11}C$.

In another aspect there is provided compounds of formula (Ia), wherein one of the composing atoms is the detectable isotope $^{18}F$.

In another aspect there is provided compounds of formula Ib:

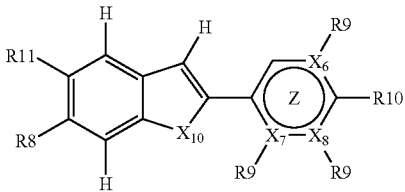

(Ib)

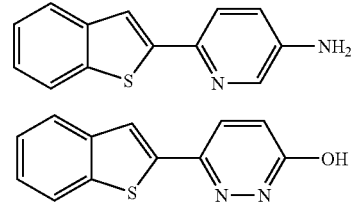

wherein
Z is a 6-membered aromatic heterocycle containing one or two N atoms, wherein $X_6$, $X_7$ and $X_8$ are independently selected from N or C, and wherein one or two of $X_6$, $X_7$ and $X_8$ is N and the remaining is C, and wherein $X_6$ is C, said C is optionally substituted with R9;

$X_{10}$ is selected from O and S;

R8 is selected from $OSi(G3)_3$, $OCH_2G4$, OG5, H, bromo, fluoro, hydroxy, methoxy, $Sn(C_{1-4}$ alkyl$)_3$, $N(CH_3)_3^+$, $IG6^+$, $N_2^+$ and nitro;

R9 is selected from H, bromo, fluoro, $Sn(C_{1-4}$ alkyl$)_3$, $N(CH_3)_3^+$, $IG6^+$, $N_2^+$ and nitro;

R10 is selected from amino, methylamino, $NH(CH_2)_{2-4}G7$, dimethylamino, methoxy, hydroxy, $(CO)NH_2$ and $O(CH_2)_{2-4}G7$;

R11 is selected from $OSi(G3)_3$, $OCH_2G4$, OG5, H, bromo, fluoro, hydroxy, methoxy, $Sn(C_{1-4}$ alkyl$)_3$, $N(CH_3)_3^+$, $IG6^+$, $N_2^+$ and nitro;

G3 is selected from $C_{1-4}$ alkyl and phenyl;

G4 is selected from 2-(trimethylsilyl)ethoxy, $C_{1-3}$ alkoxy, 2-($C_{1-3}$ alkoxy)ethoxy, $C_{1-3}$ alkylthio, cyclopropyl, vinyl, phenyl, p-methoxyphenyl, o-nitrophenyl, and 9-anthryl;

G5 is selected from tetrahydropyranyl, 1-ethoxyethyl, phenacyl, 4-bromophenacyl, cyclohexyl, t-butyl, t-butoxycarbonyl, 2,2,2-trichloroethylcarbonyl and triphenylmethyl;

$IG6^+$ is a constituent of a iodonium salt, in which the iodo atom is hyper-valent and has a positive formal charge and, in which, G6 is phenyl, optionally substituted with one substituent selected from methyl and bromo;

G7 is selected from bromo, iodo, $OSO_2CF_3$, $OSO_2CH_3$ and $OSO_2phenyl$, said phenyl being optionally substituted with methyl or bromo;

with reference to formula Ib, one or several of the substituents selected from R8, R9, R10 and R11 is one of the functional groups selected from bromo, fluoro, hydroxy, $Sn(C_{1-4}$ alkyl$)_3$, $N(CH_3)_3^+$, $IG6^+$, $N_2^+$, nitro, amino, methylamino, $NH(CH_2)_{2-4}G7$;

as a free base or a salt, solvate or solvate of a salt thereof;

with the provisio that the following compounds are excluded:

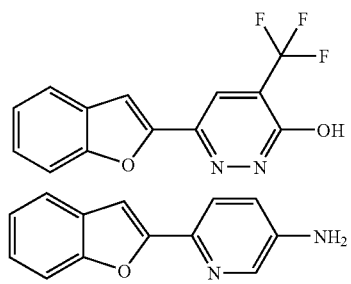

In another aspect there is provided compounds of formula Ib, wherein $X_7$ is C, said C is optionally substituted with R9, and wherein $X_8$ is C, said C is optionally substituted with R9.

In another aspect there is provided compounds of formula Ib, wherein R9 is selected from H, bromo, fluoro, chloro, iodo, $Sn(C_{1-4}$ alkyl$)_3$, $N(CH_3)_3^+$, $IG6^+$, $N_2^+$ and nitro.

In another aspect there is provided compounds of formula Ib, wherein with reference to formula Ib, one or several of the substituents selected from R8, R9, R10 and R11 is one of the functional groups selected from bromo, fluoro, hydroxy, $Sn(C_{1-4}$ alkyl$)_3$, $N(CH_3)_3^+$, $IG6^+$, $N_2^+$, nitro, amino, methylamino, $NH(CH_2)_{2-4}G7$, $N(CH_3)CHO$, $N(CH_3)COCH_3$, $N(CH_3)CO_2$-t-butyl, $(CO)NH_2$, $O(CH_2)_{2-4}G7$, $OSi(G3)_3$ and $OCH_2G4$.

In another aspect there is provided compounds of formula Ib, wherein R10 is selected from amino, methylamino, $NH(CH_2)_{2-4}G7$, dimethylamino, $N(CH_3)CHO$, $N(CH_3)COCH_3$, $N(CH_3)CO_2$-t-butyl, methoxy, hydroxy, $(CO)NH_2$ and $O(CH_2)_{2-4}G7$;

In another aspect there is provided compounds of formula Ib, wherein R8 is H; R10 is selected from amino, methylamino, dimethylamino and $NH(CH_2)_{2-4}G7$; R11 is selected from $OSi(CH_3)_2C(CH_3)_3$, H, fluoro, hydroxy, methoxy, $Sn(C_{1-4}$ alkyl$)_3$ and $N_2^+$.

In another aspect there is provided compounds of formula Ib, wherein R8 is H; R9 is H, F, $NO_2$; R10 is selected from amino, methylamino, dimethylamino, $NH(CH_2)_{2-4}G7$, $N(CH_3)CHO$, $N(CH_3)COCH_3$, $N(CH_3)CO_2$-t-butyl, $(CO)NH_2$ and $O(CH_2)_{2-4}G7$; R11 is selected from $OSi(CH_3)_2C(CH_3)_3$, H, fluoro, hydroxy, methoxy, $OCH_2G4$, $Sn(C_{1-4}$ alkyl$)_3$ and $N_2^+$.

In another aspect there is provided compounds of formula Ib, wherein Z is a pyridine ring, wherein $X_6$ and $X_7$ are C, and wherein $X_8$ is N.

In another aspect there is provided compounds of formula Ib, wherein Z is a pyridine ring, wherein $X_6$ and $X_8$ are C, and wherein $X_7$ is N.

In another aspect there is provided compounds of formula Ib, wherein Z is a pyrimidine ring, wherein $X_6$ and $X_8$ are N, and wherein $X_7$ is C.

In another aspect there is provided compounds of formula Ib, wherein Z is a pyrazine ring, wherein $X_6$ and $X_7$ are N, and wherein $X_8$ is C.

In another aspect there is provided compounds of formula Ib, wherein Z is a pyridazine ring, wherein $X_7$ and $X_8$ are N, and wherein $X_6$ is C.

In another aspect there is provided compounds of formula Ib, said compound being:

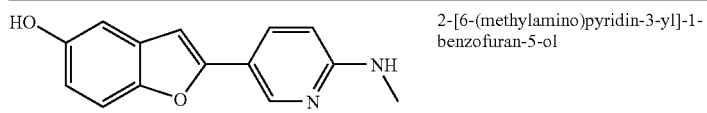
2-[6-(methylamino)pyridin-3-yl]-1-benzofuran-5-ol

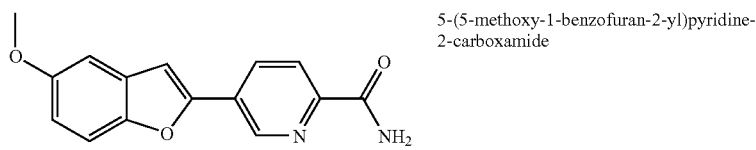
5-(5-methoxy-1-benzofuran-2-yl)pyridine-2-carboxamide

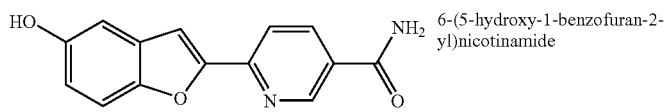
6-(5-hydroxy-1-benzofuran-2-yl)nicotinamide

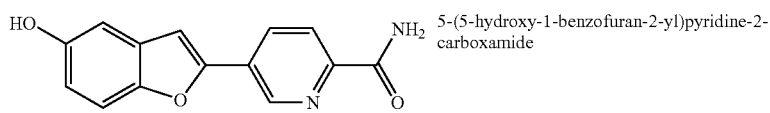
5-(5-hydroxy-1-benzofuran-2-yl)pyridine-2-carboxamide

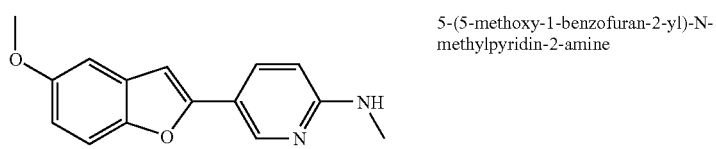
5-(5-methoxy-1-benzofuran-2-yl)-N-methylpyridin-2-amine

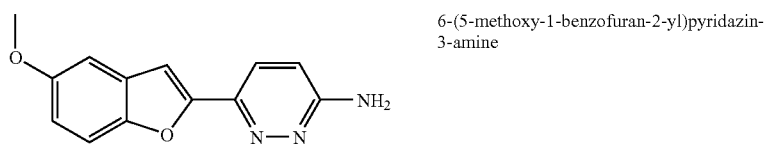
6-(5-methoxy-1-benzofuran-2-yl)pyridazin-3-amine

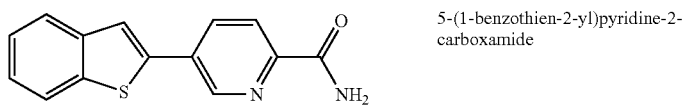
5-(1-benzothien-2-yl)pyridine-2-carboxamide

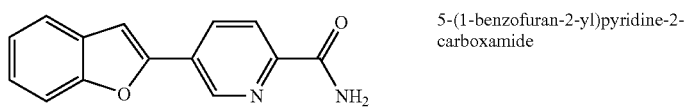
5-(1-benzofuran-2-yl)pyridine-2-carboxamide

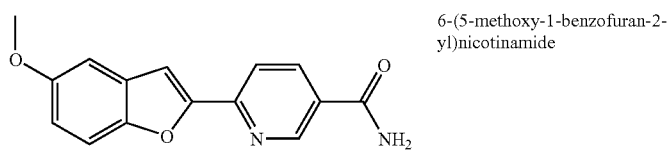
6-(5-methoxy-1-benzofuran-2-yl)nicotinamide

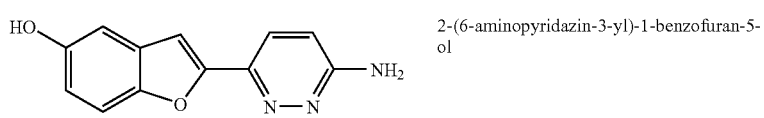
2-(6-aminopyridazin-3-yl)-1-benzofuran-5-ol

In another aspect there is provided compounds of formula Ib, said compound being:

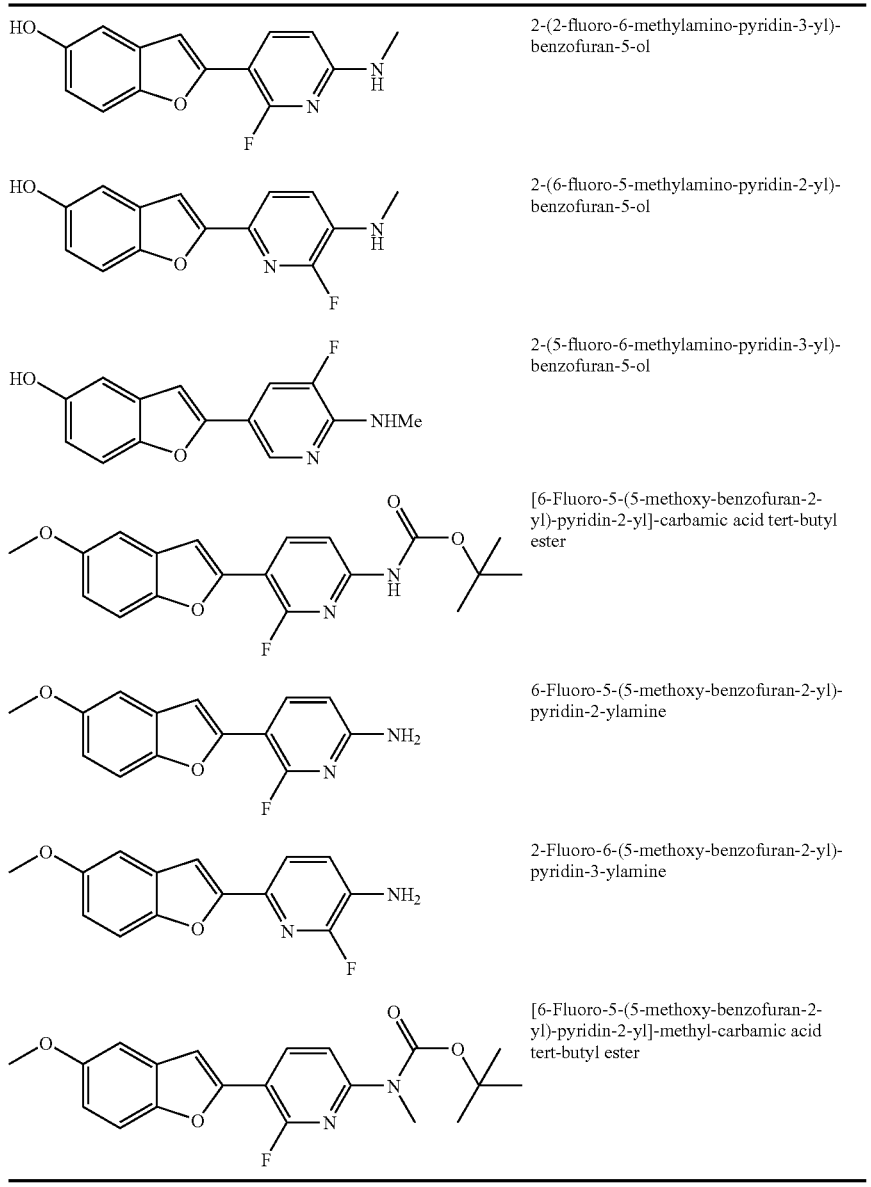

2-(2-fluoro-6-methylamino-pyridin-3-yl)-benzofuran-5-ol 2-(6-fluoro-5-methylamino-pyridin-2-yl)-benzofuran-5-ol 2-(5-fluoro-6-methylamino-pyridin-3-yl)-benzofuran-5-ol

[6-Fluoro-5-(5-methoxy-benzofuran-2-yl)-pyridin-2-yl]-carbamic acid tert-butyl ester 6-Fluoro-5-(5-methoxy-benzofuran-2-yl)-pyridin-2-ylamine 2-Fluoro-6-(5-methoxy-benzofuran-2-yl)-pyridin-3-ylamine

[6-Fluoro-5-(5-methoxy-benzofuran-2-yl)-pyridin-2-yl]-methyl-carbamic acid tert-butyl ester In another aspect there is provided use of compounds of formula Ib, as synthetic precursor in a process for preparation of a labeled compound, wherein the said label is constituted by one [$^{11}$C]methyl group.

In another aspect there is provided use of compounds of formula Ib, as synthetic precursor in a process for preparation of a labeled compound, wherein the said label is constituted by one $^{18}$F atom.

In another aspect there is provided use of compounds of formula Ib, as synthetic precursor in a process for preparation of a labeled compound, wherein the said label is constituted by one atom selected from $^{120}$I, $^{123}$I, $^{125}$I and $^{131}$I.

In another aspect there is provided a pharmaceutical composition comprising a compound according to formula (Ia), together with a pharmaceutically acceptable carrier.

In another aspect there is provided a pharmaceutical composition for in vivo imaging of amyloid deposits, comprising a radio-labeled compound according to formula (Ia), together with a pharmaceutically acceptable carrier.

In another aspect there is provided an in vivo method for measuring amyloid deposits in a subject, comprising the steps of: (a) administering a detectable quantity of a to pharmaceutical composition comprising a radio-labeled compound according to formula (Ia), and (b): detecting the binding of the compound to amyloid deposit in the subject.

In one embodiment of this aspect, said detection is carried out by the group of techniques selected from gamma imaging, magnetic resonance imaging and magnetic resonance spectroscopy.

In another embodiment of this aspect, said subject is suspected of having a disease or syndrome selected from the group consisting of Alzheimer's Disease, familial Alzheimer's Disease, Down's Syndrome and homozygotes for the apolipoprotein E4 allele.

In another aspect there is provided a compound of formula (Ia) for use in therapy. In another aspect there is provided use of a compound of formula (Ia), in the manufacture of a medicament for prevention and/or treatment of Alzheimer's Disease, familial Alzheimer's Disease, Down's Syndrome and homozygotes for the apolipoprotein E4 allele.

In another aspect there is provided a method of prevention and/or treatment of Alzheimer's Disease, familial Alzheimer's Disease, Down's Syndrome and homozygotes for the apolipoprotein E4 allele, comprising administrering to a mammal, including man in need of such prevention and/or treatment, a therapeutically effective amount of a compound of formula (Ia).

Definitions

As used herein, "alkyl", "alkylenyl" or "alkylene" used alone or as a suffix or prefix, is intended to include both branched and straight chain saturated aliphatic hydrocarbon groups having from 1 to 12 carbon atoms or if a specified number of carbon atoms is provided then that specific number would be intended. For example "$C_{1-6}$ alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "$N(C_0 \text{ alkyl})_2$" is equivalent to "$NH_2$" (amino). When the specific number denoting the alkylenyl or alkylene-group is the integer 0 (zero), a bond is intended to link the groups onto which the alkylenyl or alkylene-group is substituted. For example, "$NH(C_0 \text{ alkylene})NH_2$" is equivalent to "$NHNH_2$" (hydrazino). As used herein, the groups linked by an alkylene or alkylenyl-group are intended to be attached to the first and to the last carbon of the alkylene or alkylenyl-group. In the case of methylene, the first and the last carbon is the same. For example, "$N(C_4 \text{ alkylene})$", "$N(C_5 \text{ alkylene})$" and "$N(C_2 \text{ alkylene})_2NH$" is equivalent to pyrrolidinyl, piperidinyl and piperazinyl, respectively.

Examples of alkyl include, but are not limited to, methyl, ethyl, n-propyl, i-propyl, n-butyl, i-butyl, sec-butyl, t-butyl, pentyl, and hexyl.

Examples of alkylene or alkylenyl include, but are not limited to, methylene, ethylene, propylene, and butylene.

As used herein, "alkoxy" or "alkyloxy" represents an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, "fluoroalkyl", "fluoroalkylene" and "fluoroalkoxy", used alone or as a suffix or prefix, refers to groups in which one, two, or three of the hydrogen(s) attached to the carbon(s) of the corresponding alkyl, alkylene and alkoxy-groups are replaced by fluoro. Examples of fluoroalkyl include, but are not limited to, trifluoromethyl, difluoromethyl, fluoromethyl, 2,2,2-trifluoroethyl, 2-fluoroethyl and 3-fluoropropyl.

Examples of fluoroalkylene include, but are not limited to, difluoromethylene, fluoromethylene, 2,2-difluorobutylene and 2,2,3-trifluorobutylene.

Examples of fluoroalkoxy include, but are not limited to, trifluoromethoxy, 2,2,2-trifluoroethoxy, 3,3,3-trifluoropropoxy and 2,2-difluoropropoxy.

As used herein, "aromatic" refers to hydrocarbonyl groups having one or more unsaturated carbon ring(s) having aromatic characters, (e.g. 4n+2 delocalized electrons where "n" is an integer) and comprising up to about 14 carbon atoms. In addition "heteroaromatic" refers to groups having one or more unsaturated rings containing carbon and one or more heteroatoms such as nitrogen, oxygen or sulphur having aromatic character (e.g. 4n+2 delocalized electrons).

As used herein, the term "aryl" refers to an aromatic ring structure made up of from 5 to 14 carbon atoms. Ring structures containing 5, 6, 7 and 8 carbon atoms would be single-ring aromatic groups, for example, phenyl. Ring structures containing 8, 9, 10, 11, 12, 13, or 14 would be polycyclic, for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls. The terms ortho, meta and para apply to 1,2-, 1,3- and 1,4-disubstituted benzenes, respectively. For example, the names 1,2-dimethylbenzene and ortho-dimethylbenzene are synonymous.

As used herein, the term "cycloalkyl" is intended to include saturated ring groups, having the specified number of carbon atoms. These may include fused or bridged polycyclic systems. Preferred cycloalkyls have from 3 to 10 carbon atoms in their ring structure, and more preferably have 3, 4, 5, and 6 carbons in the ring structure. For example, "$C_{3-6}$ cycloalkyl" denotes such groups as cyclopropyl, cyclobutyl, cyclopentyl, or cyclohexyl.

As used herein, "halo" or "halogen" refers to fluoro, chloro, bromo, and iodo. "Counterion" is used, for example, to represent a small, negatively charged species such as chloride, bromide, hydroxide, acetate, sulfate, tosylate, benezensulfonate, and the like.

As used herein, the term "heterocyclyl" or "heterocyclic" or "heterocycle" refers to a saturated, unsaturated or partially saturated, monocyclic, bicyclic or tricyclic ring (unless otherwise stated) containing 3 to 20 atoms of which 1, 2, 3, 4 or 5 ring atoms are chosen from nitrogen, sulphur or oxygen, which may, unless otherwise specified, be carbon or nitrogen linked, wherein a —$CH_2$— group is optionally replaced by a —$C(O)$—; and where unless stated to the contrary a ring nitrogen or sulphur atom is optionally oxidised to form the N-oxide or S-oxide(s) or a ring nitrogen is optionally quarternized; wherein a ring —NH is optionally substituted by acetyl, formyl, methyl or mesyl; and a ring is optionally substituted by one or more halo. It is understood that when the total number of S and O atoms in the heterocyclyl exceeds 1, then these heteroatoms are not adjacent to one another. If the said heterocyclyl group is bi- or tricyclic then at least one of the rings may optionally be a heteroaromatic or aromatic ring provided that at least one of the rings is non-heteroaromatic. If the said heterocyclyl group is monocyclic then it must not be aromatic. Examples of heterocyclyls include, but are not limited to, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, tetrahydroisoquinolinyl, tetrahydroquinolinyl, indolinyl, tetrahydropyranyl, dihydro-2H-pyranyl, tetrahydrofuranyl and 2,5-dioxoimidazolidinyl.

As used herein, "heteroaryl" refers to a heteroaromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like.

As used herein, the phrase "protecting group" or "protective group" means temporary substituents which protect a potentially reactive functional group from undesired chemical transformations. Examples of such protecting groups include esters of carboxylic acids, silyl ethers of alcohols, and acetals and ketals of aldehydes and ketones, respectively. A sub-group of protecting groups are those that protect a nucleophilic group (e.g. an aromatic hydroxy group) against alkylation and thus permit selective N-alkylation of an amino-group present in the same molecule under basic conditions. Examples of such protecting groups include, but is not limited to, methyl, 2-(trimethylsilyl)ethoxymethyl, alkoxymethyl and t-butyldimethylsilyl.

As used herein, "pharmaceutically acceptable" is employed to refer to those compounds, materials, compositions, and/or dosage forms which are, within the scope of sound medical judgment, suitable for use in contact with the tissues of human beings and animals without excessive toxicity, irritation, allergic response, or other problem or complication and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, phosphoric, and the like; and the salts prepared from organic acids such as lactic, maleic, citric, benzoic, methanesulfonic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are used.

As used herein, "in vivo hydrolysable precursors" means an in vivo hydrolysable (or cleavable) ester of a compound of the invention that contains a carboxy or a hydroxy group. For example amino acid esters, $C_{1-6}$ alkoxymethyl esters like methoxymethyl; $C_{1-6}$alkanoyloxymethyl esters like pivaloyloxymethyl; $C_{3-8}$cycloalkoxycarbonyloxy $C_{1-6}$alkyl esters like 1-cyclohexylcarbonyloxyethyl, acetoxymethoxy, or phosphoramidic cyclic esters.

As used herein, "tautomer" means other structural isomers that exist in equilibrium resulting from the migration of a hydrogen atom. For example, keto-enol tautomerism where the resulting compound has the properties of both a ketone and an unsaturated alcohol.

As used herein "stable compound" and "stable structure" are meant to indicate a compound that is sufficiently robust to survive isolation to a useful degree of purity from a reaction mixture, and subsequent prolonged storage in the cold or at ambient temperature, and optionally formulated into an efficacious therapeutic or diagnostic agent.

Compounds of the invention further include hydrates and solvates.

The present invention includes isotopically labeled compounds of the invention. An "isotopically-labeled", "radiolabeled", "labeled", "detectable" or "detectable amyloid binding" compound, or a "radioligand" is a compound of the invention where one or more atoms are replaced or substituted by an atom having an atomic mass or mass number different from the atomic mass or mass number typically found in nature (i.e., naturally occurring). One non-limiting exception is $^{19}F$, which allows detection of a molecule which contains this element without enrichment to a higher degree than what is naturally occurring. Compounds carrying the substituent $^{19}F$ may thus also be referred to as "labeled" or the like. Suitable radionuclides (i.e. "detectable isotopes") that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. It is to be understood that an isotopically labeled compound of the invention need only to be enriched with a detectable isotop to, or above, the degree which allows detection with a technique suitable for the particular application, e.g. in a detectable compound of the invention labeled with $^{11}C$, the carbon-atom of the labeled group of the labeled compound may be constituted by $^{12}C$ or other carbon-isotopes in a fraction of the molecules. The radionuclide that is incorporated in the instant radiolabeled compounds will depend on the specific application of that radiolabeled compound. For example, for in vitro plaque or receptor labeling and competition assays, compounds that incorporate $^{3}H$, $^{14}C$, or $^{125}I$ will generally be most useful. For in vivo imaging applications $^{11}C$, $^{13}C$, $^{18}F$, $^{19}F$, $^{120}I$, $^{123}I$, $^{131}I$, $^{75}Br$, or $^{76}Br$ will generally be most useful.

Examples of an "effective amount" include amounts that enable imaging of amyloid deposit(s) in vivo, that yield acceptable toxicity and bioavailability levels for pharmaceutical use, and/or prevent cell degeneration and toxicity associated with fibril formation.

This invention also provides radiolabeled 2-heteroaryl substituted benzothiophene and benzofurane derivatives as amyloid imaging agents and synthetic precursor compounds from which such are prepared.

Methods of Use

The compounds of the present invention may be used to determine the presence, location and/or amount of one or more amyloid deposit(s) in an organ or body area, including the brain, of an animal or human. Amyloid deposit(s) include, without limitation, deposit(s) of Aβ. In allowing the temporal sequence of amyloid deposition to be followed, the inventive compounds may farther be used to correlate amyloid deposition with the onset of clinical symptoms associated with a disease, disorder or condition. The inventive compounds may ultimately be used to treat, and to diagnose a disease, disorder or condition characterized by amyloid deposition, such as AD, familial AD, Down's syndrome, amyloidosis and homozygotes for the apolipoprotein E4 allele.

The method of this invention determines the presence and location of amyloid deposits in an organ or body area, preferably brain, of a patient. The present method comprises administration of a detectable quantity of a pharmaceutical composition containing an amyloid-binding compound of the present invention called a "detectable compound," or a pharmaceutically acceptable water-soluble salt thereof, to a patient. A "detectable quantity" means that the amount of the detectable compound that is administered is sufficient to enable detection of binding of the compound to amyloid. An "imaging effective quantity" means that the amount of the detectable compound that is administered is sufficient to enable imaging of binding of the compound to amyloid.

The invention employs amyloid probes which, in conjunction with non-invasive neuroimaging techniques such as magnetic resonance spectroscopy (MRS) or imaging (MINI), or gamma imaging such as positron emission tomography (PET) or single-photon emission computed tomography (SPECT), are used to quantify amyloid deposition in vivo. The term "in vivo imaging", or "imaging", refers to any method which permits the detection of a labeled heteroaryl substituted benzofuran or benzothiophene derivatives as described herein. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound. A "subject" is a mammal, preferably a human, and most preferably a human suspected of having dementia.

For purposes of in vivo imaging, the type of detection instrument available is a major factor in selecting a given label. For instance, radioactive isotopes and $^{19}F$ are particularly suitable for in vivo imaging in the methods of the present invention. The type of instrument used will guide the selection of the radionuclide or stable isotope. For instance, the radionuclide chosen must have a type of decay detectable by a given type of instrument.

Another consideration relates to the half-life of the radionuclide. The half-life should be long enough so that it is still detectable at the time of maximum uptake by the target, but short enough so that the host does not sustain deleterious radiation. The radiolabeled compounds of the invention can be detected using gamma imaging wherein emitted gamma irradiation of the appropriate wavelength is detected. Methods of gamma imaging include, but are not limited to, SPECT and PET. Preferably, for SPECT detection, the chosen radiolabel will lack a particulate emission, but will produce a large number of photons in a 140-200 keV range.

For PET detection, the radiolabel will be a positron-emitting radionuclide, such as $^{18}F$ or $^{11}C$, which will annihilate to form two gamma rays which will be detected by the PET camera.

In the present invention, amyloid binding compounds/probes are made which are useful for in vivo imaging and quantification of amyloid deposition. These compounds are to be used in conjunction with non-invasive neuroimaging techniques such as magnetic resonance spectroscopy (MRS) or imaging (MRI), positron emission tomography (PET), and single-photon emission computed tomography (SPECT). In accordance with this invention, the 2-heteroaryl substituted benzothiophene and benzofurane derivatives may be labeled with $^{19}F$ or $^{13}C$ for MRS/MRI by general organic chemistry techniques known in the art. The compounds may also be radiolabeled with, for example, $^{18}F$, $^{11}C$, $^{75}Br$, $^{76}Br$, or $^{120}I$ for PET by techniques well known in the art and are described by Fowler, J. and Wolf, A. in "Positron Emission Tomography and Autoradiography" 391-450 (Raven Press, 1986). The compounds may also be radiolabeled with $^{123}I$ and $^{131}I$ for SPECT by any of several techniques known to the art. See, e.g., Kulkami, Int. J. Rad. Appl. &Inst. (Part B) 18: 647 (1991). The compounds may also be radiolabeled with known metal radiolabels, such as Technetium-99m ($^{99m}Tc$). Modification of the substituents to introduce ligands that bind such metal ions can be effected without undue experimentation by one of ordinary skill in the radiolabeling art. The metal radiolabeled compound can then be used to detect amyloid deposits. Preparing radiolabeled derivatives of Tc-99m is well known in the art. See, for example, Zhuang et al. Nuclear Medicine & Biology 26(2):217-24, (1999); Oya et al. Nuclear Medicine &Biology 25(2):135-40, (1998), and Hom et al. Nuclear Medicine &Biology 24(6):485-98, (1997). In addition, the compounds may be labeled with $^3H$, $^{14}C$ and $^{125}I$, by methods well known to the one skilled in the art, for detection of amyloid plaque in in vitro and post mortem samples. Furthermore, fluorescent compounds of the present invention may be used for the detection of plaques present in in vitro and post mortem samples by employment of well-known techniques based on the detection of fluorescence.

The methods of the present invention may use isotopes detectable by nuclear magnetic resonance spectroscopy for purposes of in vivo imaging and spectroscopy. Elements particularly useful in magnetic resonance spectroscopy include $^{19}F$ and $^{13}C$.

Suitable radioisotopes for purposes of this invention include beta-emitters, gamma-emitters, positron-emitters, and x-ray emitters. These radioisotopes include $^{120}I$, $^{123}I$, $^{131}I$, $^{125}I$, $^{18}F$, $^{11}C$, $^{75}Br$, and $^{76}Br$. Suitable stable isotopes for use in Magnetic Resonance Imaging (MRI) or Spectroscopy (MRS), according to this invention, include $^{19}F$ and $^{13}C$. Suitable radioisotopes for in vitro quantification of amyloid in homogenates of biopsy or post-mortem tissue include $^{125}I$, $^{14}C$, and $^3H$. The preferred radiolabels are $^{11}C$ and $^{18}F$ for use in PET in vivo imaging, $^{123}I$ for use in SPECT imaging, $^{19}F$ for MRS/MRI, and $^3H$ and $^{14}C$ for in vitro studies. However, any conventional method for visualizing diagnostic probes can be utilized in accordance with this invention.

The compounds of the present invention may be administered by any means known to one of ordinary skill in the art. For example, administration to the animal may be local or systemic and accomplished orally, parenterally, by inhalation spray, topically, rectally, nasally, buccally, vaginally, or via an implanted reservoir. The term "parenteral" as used herein includes subcutaneous, intravenous, intraarterial, intramuscular, intraperitoneal, intrathecal, intraventricular, intrasternal, intracranial, and intraosseous injection and infusion techniques.

The exact administration protocol will vary depending upon various factors including the age, body weight, general health, sex and diet of the patient; the determination of specific administration procedures would be routine to any one of ordinary skill in the art.

Dose levels on the order of about 0.001 µg/kg/day to about 10,000 mg/kg/day of an inventive compound are useful for the inventive methods. In one embodiment, the dose level is about 0.001 µg/kg/day to about 10 g/kg/day. In another embodiment, the dose level is about 0.01 µg/kg/day to about 1.0 g/kg/day. In yet another embodiment, the dose level is about 0.1 mg/kg/day to about 100 mg/kg/day.

The specific dose level for any particular patient will vary depending upon various factors, including the activity and the possible toxicity of the specific compound employed; the age, body weight, general health, sex and diet of the patient; the time of administration; the rate of excretion; the drug combination; and the form of administration. Typically, in vitro dosage-effect results provide useful guidance on the proper doses for patient administration. Studies in animal models are also helpful. The considerations for determining the proper dose levels are well known in the art and within the skills of an ordinary physician.

Any known administration regimen for regulating the timing and sequence of drug delivery may be used and repeated as necessary to effect treatment in the inventive methods.

The regimen may include pretreatment and/or co-administration with additional therapeutic agent(s).

In one embodiment, the inventive compounds are administered to an animal that is suspected of having or that is at risk of developing a disease, disorder or condition characterized by amyloid deposition. For example, the animal may be an elderly human.

In another embodiment, compounds and methods for their preparation, useful as precursors, are provided. Such precursors may be used as synthetic starting materials for the incorporation of labeled molecular fragments leading to radiolabeled 2-heteroaryl substituted benzothiophene and benzofuran derivatives as amyloid imaging agents.

Method for Detecting Amyloid Deposits in vitro

This invention further provides a method for detecting amyloid deposit(s) in vitro comprising: (i) contacting a bodily tissue with an effective amount of an inventive compound, wherein the compound would bind any amyloid deposit(s) in the tissue; and (ii) detecting binding of the compound to amyloid deposit(s) in the tissue.

The binding may be detected by any means known in the art. Examples of detection means include, without limitation, microscopic techniques, such as bright-field, fluorescence, laser-confocal and cross-polarization microscopy.

Pharmaceutical Compositions

This invention further provides a pharmaceutical composition comprising: (i) an effective amount of at least one inventive compound; and (ii) a pharmaceutically acceptable carrier.

The composition may comprise one or more additional pharmaceutically acceptable ingredient(s), including without limitation one or more wetting agent(s), buffering agent(s), suspending agent(s), lubricating agent(s), emulsifier(s), disintegrant(s), absorbent(s), preservative(s), surfactant(s), colorant(s), flavorant(s), sweetener(s) and therapeutic agent(s).

The composition may be formulated into solid, liquid, gel or suspension form for: (1) oral administration as, for example, a drench (aqueous or non-aqueous solution or suspension), tablet (for example, targeted for buccal, sublingual or systemic absorption), bolus, powder, granule, paste for application to the tongue, hard gelatin capsule, soft gelatin capsule, mouth spray, emulsion and microemulsion; (2) parenteral administration by subcutaneous, intramuscular, intravenous or epidural injection as, for example, a sterile solution, suspension or sustained-release formulation; (3) topical application as, for example, a cream, ointment, controlled-release patch or spray applied to the skin; (4) intravaginal or intrarectal administration as, for example, a pessary, cream or foam; (5) sublingual administration; (6) ocular administration; (7) transdermal administration; or (8) nasal administration.

In one embodiment, the composition is formulated for intravenous administration and the carrier includes a fluid and/or a nutrient replenisher. In another embodiment, the composition, is capable of binding specifically to amyloid in vivo, is capable of crossing the blood-brain barrier, is non-toxic at appropriate dose levels and/or has a satisfactory duration of effect. In yet another embodiment, the composition comprises about 10 mg of human serum albumin and from about 0.0005 to 500 mg of a compound of the present invention per mL of phosphate buffer containing NaCl.

The present invention further provides compositions comprising a compound of formula Ia, and at least one pharmaceutically acceptable carrier, diluent or excipient.

The present invention further provides methods of treating or preventing an Aβ-related pathology in a patient, comprising administering to the patient a therapeutically effective amount of a compound of formula Ia.

The present invention further provides a compound described herein for use as a medicament.

The present invention further provides a compound described herein for the manufacture of a medicament.

Some compounds of formula Ia and Ib may have stereogenic centres and/or geometric isomeric centres (E- and Z-isomers), and it is to be understood that the invention encompasses all such optical isomers, enantiomers, diastereoisomers, atropisomers and geometric isomers.

The present invention relates to the use of compounds of formula Ia as hereinbefore defined as well as to the salts thereof. Salts for use in pharmaceutical compositions will be pharmaceutically acceptable salts, but other salts may be useful in the production of the compounds of formula Ia.

Compounds of the invention can be used as medicaments. In some embodiments, the present invention provides compounds of formula Ia, or pharmaceutically acceptable salts, tautomers or in vivo-hydrolysable precursors thereof, for use as medicaments. In some embodiments, the present invention provides compounds described herein for use as medicaments for treating or preventing an Aβ-related pathology. In some further embodiments, the Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, pre-senile dementia, senile dementia, dementia associated with Parkinson's disease, progressive supranuclear palsy or cortical basal degeneration.

Methods of Preparation

The present invention also relates to processes for preparing the compound of formula Ia and Ib as a free base, acid, or salts thereof. Throughout the following description of such processes it is to be understood that, where appropriate, suitable protecting groups will be attached to, and subsequently removed from, the various reactants and intermediates in a manner that will be readily understood by one skilled in the art of organic synthesis. Conventional procedures for using such protecting groups, as well as examples of suitable protecting groups, are described, for example, in "Protective Groups in Organic Synthesis", 3rd ed., T. W. Green, P. G. M. Wuts, Wiley-Interscience, New York (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations", 2nd ed., R. C. Larock, Wiley-VCH, New York (1999). References and descriptions of other suitable reactions are described in textbooks of organic chemistry, for example, "March's Advanced Organic Chemistry", 5th ed., M. B. Smith, J. March, John Wiley & Sons (2001) or, "Organic Synthesis", 2nd ed., M. B. Smith, McGraw-Hill, (2002). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula Ia and Ib except where defined differently. The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures. The terms "flash chromatography" or "flash column chromatography" shall mean preparative chromatography on silica using an organic solvent, or mixtures thereof, as mobile phase.

Abbreviations
Ac acetate;
atm atmosphere;
aq. aqueous;
Boc$_2$O di-tert-butyl dicarbonate;
DBU 1,8-diazobicyclo[5.4.0]undec-7-ene
DME 1,2-dimethoxyethane;
DMA N,N-dimethylacetamide;
DMF N,N-dimethylformamide;
DMSO dimethyl sulfoxide;
dppf 1,1'-bis(diphenylphosphino)ferrocene;
EtOAc ethyl acetate;
EtOH ethanol;
Et$_2$O diethylether;
h hour(s);
hep heptane;
hex hexane(s);
HPLC high performance liquid chromatography;
MeCN acetonitrile;
MeOH methanol;
o.n. over night;
NBS N-bromosuccinimide
Pd(dppf)Cl$_2$ 1,1'-bis(diphenylphosphino)ferrocene)dichloropalladium(II);
Pd(dba)$_2$ bis(dibenzylideneacetone)palladium(0);
Pd(PPh$_3$)$_2$Cl$_2$ dichlorobis(triphenylphosphine)palladium;
prep. HPLC preparative HPLC;
PTSA p-toluenesulfonic acid;
r.t. room temperature;
r.m. reaction mixture;

sat. saturated;
TBAF tetrabutylammonium fluoride;
TFA trifluoroacetic acid;
THF tetrahydrofurane;
Tos tosylate;
OTf trifluoromethanesulfonate.

Preparation of Intermediates

Compounds of formula II-VI are useful intermediates in the preparation of compound of formula Ia and Ib. Compounds of formula II-VI are either commercially available, or can be prepared from either commercially available, or in the literature described compounds. For example, compounds in which one or more of $Y_1$-$Y_3$, R1 or R2 does not correspond to the definitions of formula II-VI, can be used for the preparation of compounds of formula II-VI by transformations or introduction of substituents or groups. Such examples are given below:

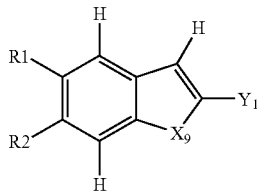

$Y_1$ = B(OH)$_2$, B(Oalkyl)$_2$, Sn(n-Bu)$_3$, Br, Cl, I, OTf

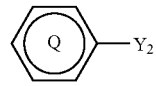

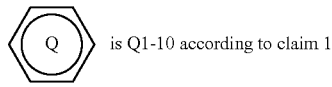

$Y_2$ = Br, Cl, I, OTf, B(OH)$_2$, B(Oalkyl)$_2$, Sn(n-Bu)$_3$, CHCH$_2$, CCH

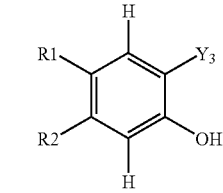

$Y_3$ = I, Br, CH$_2$COCl

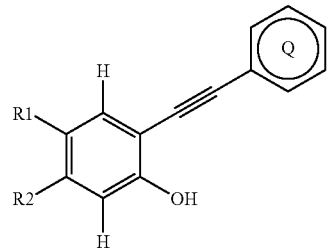

1) Preparation of Compounds of Formula II in which $Y_1$ is B(Oalkyl)$_2$ or B(OH)$_2$:

By treating the corresponding bensofuran with BuLi and quenching with trialkylborate subsequently followed by acidic hydrolysis.

From the corresponding chlorides, bromides, iodides or triflates through palladium catalysed borylation employing for example bis(pinacolato)diboran or dialkoxyboranes as reagents under palladium catalysis, using for example PdCl$_2$(dppf), or Pd(dba)$_2$ with added tricyclohexylphosphine, as catalysts, together with stoichiometric amounts of a base such as KOAc and NEt$_3$ in solvents such as DMSO, DMF, DMA or dioxan at a temperature from r.t. to 80° C., alternatively subsequently followed by acidic hydrolysis (Ishiyama et al. *Tetrahedron* 2001, 57, 9813; Murata et al. *J. Org. Chem.* 2000, 65, 164).

2) Preparation of Compounds of Formula II in WHICH Y$_1$ is Halogen:

a.) Halogenation at the 2-position of benzofuran derivatives can be obtained with tert-butyl lithium followed by treatment with I$_2$ to introduce the halogen (Zhang et al. *J. Org. Chem.* 2002, 67, 7048).

b.) From the corresponding nitro derivatives by treatment with PBr$_3$ at 175° C. (Lin, S. -Y. et al. *J. Org. Chem.* 2003, 68, 2968).

c.) By palladium-copper catalyzed reaction of compounds of formula IV with trimethylsilylacetylene.

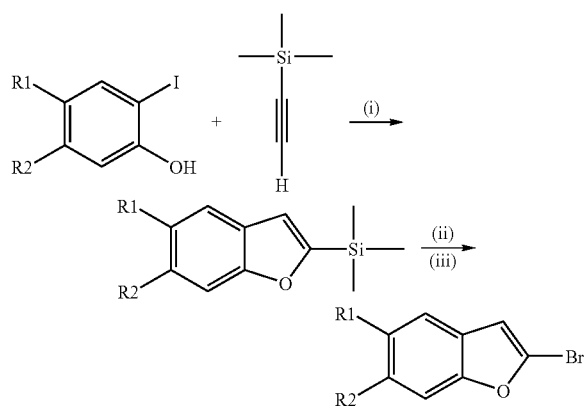

(i) Pd(Ph$_3$P)$_2$Cl$_2$/CuI, Et$_3$N/CH$_3$CN; (ii) TBAF; (iii) NBS

Subsequent removal of the TMS protecting group and halogenation with for example N-bromosuccinimide (Aquila, B. M., *Tetrahedron Lett.* 1997, 38, 2795).

3) Preparation of Compounds of Formula II in which Y$_1$ is Sn(n-Bu)$_3$, Sn(Me)$_3$ or SnPh$_3$:

a.) Introduction of a tinalkyl group can be achieved through halogen-metal exchange from the corresponding halides. Using, for example, BuLi as lithium source to treat the corresponding halogen substituted benzofurans, ie where Y$_1$=halogen. Followed by quenching with a Sn(alkyl)$_3$Cl reagent (Li, J. J. et al., *Bioorg Med. Chem.*, 2003, 11, 3777).

b.) Metallation with an alkyllithium reagent on a substrate where Y$_1$=H followed by transmetallation using a Sn(alkyl)$_3$Cl reagent affords tinylation (Einhorn et al. *Synthesis* 1984, 11, 978).

4) Preparation of Compounds of Formula IV with Y$_3$=CH$_2$COCl

The acid chloride derivatives of compounds of formula IV can be prepared via a four-step procedure from the corresponding benzyl alcohols.

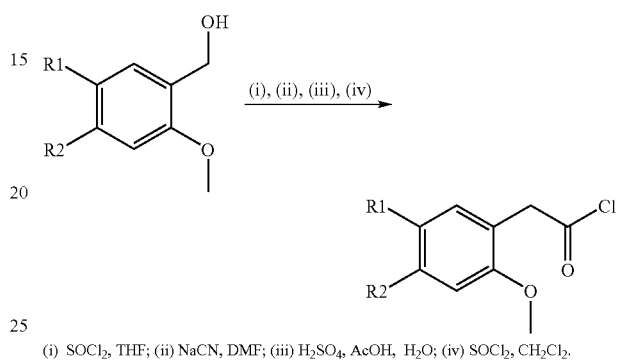

(i) SOCl$_2$, THF; (ii) NaCN, DMF; (iii) H$_2$SO$_4$, AcOH, H$_2$O; (iv) SOCl$_2$, CH$_2$Cl$_2$.

Chlorination using for example SOCl$_2$ followed by the introduction of a nitrile group. Hydrolysis of the nitrile group to the carboxylic acid followed by treatment with SOCl$_2$ affords acid chloride derivatives of formula IV (M. D. Collini et al., *Bioorg. Med. Chem. Lett.*, 2004, 14, 4925).

5) Preparation of Compounds of Formula V

By palladium-catalysed coupling of arylacetylenes of formula III with 2-iodophenols of formula IV according to standard Sonogashira conditions (Yin, Y.; Liebscher, J.; *Chem. Rev.* 2007, 107, 133).

Methods of Preparation of Non-labeled Compounds of Formula Ia and Ib

Non-limiting examples of methods for the preparation of compounds of formula Ia and Ib are given below:

1) Preparation by Palladium-catalysed Cross-coupling of Intermediates (IV) and (III) with Y$_2$=CHCH$_2$:

Palladium-catalysed coupling of styrenes and 2-hydroxyaryl halides generates a stilbene product. Alternatively, the stilbene product could be obtained by a Wittig reaction between the corresponding phosphonium bromide and aldehyde.

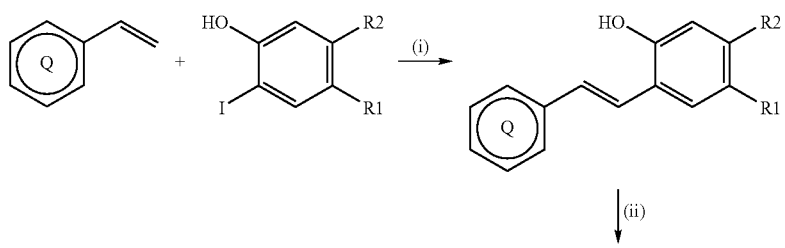

-continued

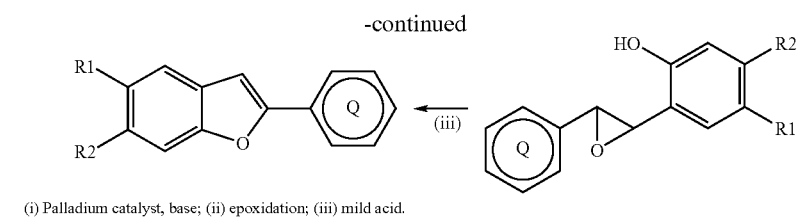

(i) Palladium catalyst, base; (ii) epoxidation; (iii) mild acid.

Epoxidation of the stilbene intermediate followed by cyclisation under mildly acidic conditions affords the benzofuran derivative (Aslam et al., *Tetrahedron*, 2006, 62, 4214).

2) Preparation by Palladium-catalysed Cross-coupling of Intermediates (IV) and (III) with $Y_2$=CCH:

Whilst the cross-coupling of ethylenes need further treatment to proceed to the benzofuran product, cross-coupling under Sonogashira conditions of hydroxyaryl iodides and the more reactive acetylenes proceeds directly to the benzofuran derivative (Aslam et al., *Tetrahedron*, 2006, 62, 4214).

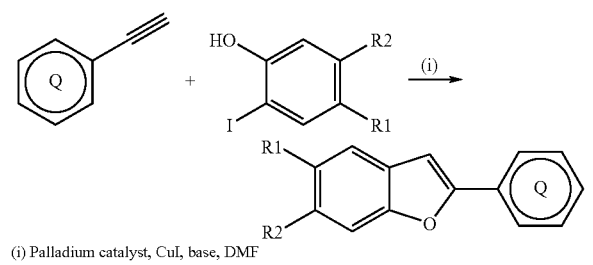

(i) Palladium catalyst, CuI, base, DMF

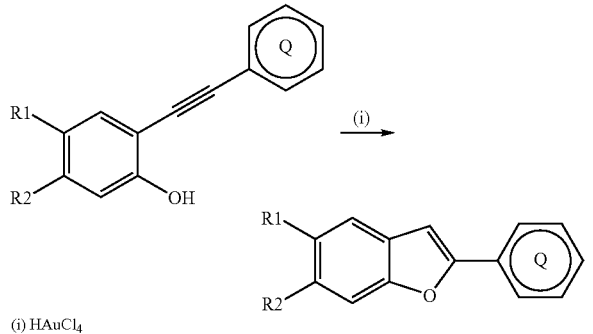

(i) HAuCl₄

When needed, the cyclisation can be induced by the use of a gold catalyst at r.t. in a solvent such as Et₂O or EtOH. The metal forms a π-complex with the alkyne which is then transformed into a σ-complex upon nucleophilic attack of the oxygen and protodemetalation affords the benzofuran product (V. Belting et al. *Org. Lett.*, 2006, 8, 4489).

3) Preparation from Intermediate (III):

A Freidel-Craft reaction between the appropriate Q and acetyl chloride derivatives of formula III followed by deprotection, with for example pyridine hydrobromide, at high temperature results in cyclisation and affords compounds of formula I (M. D. Collini et al., *Bioorg. Med. Chem. Lett.*, 2004, 14, 4925).

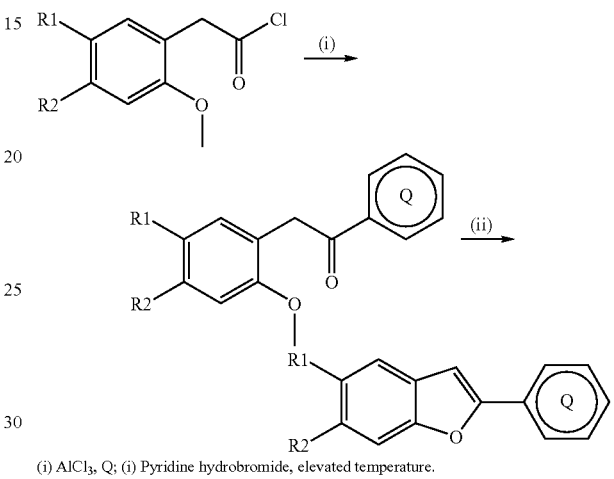

(i) AlCl₃, Q; (i) Pyridine hydrobromide, elevated temperature.

4) Preparation by Palladium-catalysed Cross-coupling of Intermediates (II) and (III):

Palladium-catalysed Suzuki- or Stille coupling of aryl halides, or pseudo-halides, of intermediates of formula III (e.g. $Y_2$=Cl, Br, I or triflate) with boronic acids or esters of formula II (e.g. $Y_1$=B(OH)₂ or B(Oalkyl)₂) or stannanes of formula II (e.g. $Y_1$=Sn(n-Bu)₃). A palladium catalyst such as Pd(dppf)Cl₂ or Pd(PPh₃)Cl₂ may be used in a solvent such as DMF or EtOH at a temperature of e.g. 80° C. (Kotha et al. *Tetrahedron* 2002, 58, 9633-9695; Suzuki *J. Organomet. Chem.* 1999, 576, 147-168; Fugami et al. *Top. Curr. Chem.* 2002, 219, 87-130.)

Methods of Preparation of Labeled Compounds of Formula Ia

In general, the same synthetic reactions used for the assembly of non-labeled compounds of formula Ia from non-labeled reagents or intermediates, can be employed for the analogous incorporation of a detectable isotope by use of the corresponding labeled reagents or intermediates.

It is preferred to introduce the label at a late stage of the synthesis toward compounds of formula Ia, especially if the label is an isotope with relatively short half-life, such as $^{11}C$. Most preferred is to do this introduction as the last synthetic step.

Several useful reagents, synthons or intermediates labeled with long-lived or non-radioactive isotopes, including for example [$^{2/3}H$]H₂, [$^{2/3}H$]CH₃I, [$^{13/14}C$]CH₃I, [$^{13/14}C$]CN⁻, [$^{13/14}C$]CO₂ are commercially available and can, if needed, be further synthetically transformed by conventional synthetic methods. Reagents labeled with relatively more short-lived isotopes, such as $^{11}C$ and $^{18}F$, are generated by a cyclotron, followed by suitable trapping and optionally further synthetic manipulations to provide the desired reagent. The generation and the synthetic manipulations of labeled reagents and intermediates, and the use and chemistries of these precursors for the synthesis of more complex labeled molecules, is well known to the one skilled in the art of radio-synthesis and labeling and is reviewed in the literature (Langstrom et al. Acta Chem. Scand. 1999, 53, 651). For additional references see for example: Ali et al. Synthesis 1996, 423 for labeling with halogens; Antoni G., Kihlberg T., and Långström B. (2003) Handbook of nuclear chemistry, edited by Vertes A., Nagy S., and Klenscar Z., Vol. 4, 119-165 for labeling for PET-applications; Saljoughian et al. Synthesis 2002, 1781 for labeling with $^3$H; McCarthy et al. Curr. Pharm. Des. 2000, 6, 1057 for labeling with $^{14}$C.

Detectable isotopes, useful for the labeling of compounds of formula Ia as defined herein include, for use in PET: $^{11}$C, $^{18}$F, $^{75}$Br, $^{76}$Br and $^{120}$I, for use in SPECT: $^{123}$I and $^{131}$I, for MRI-applications: $^{19}$F and $^{13}$C, for detection in in-vitro and post-mortem samples: $^3$H, $^{14}$C and $^{125}$I. The most useful isotopes for labeling are $^{11}$C, $^{18}$F, $^{123}$I, $^{19}$F, $^3$H and $^{14}$C.

Below follow non-limiting descriptions on processes for the preparation of labeled compounds of formula Ia:

Compounds of formula Ia and Ib, which carry a hydroxy-, amino- or aminoalkyl group are useful precursors for O- and N-alkylation, respectively, with a labeled alkylating agent, such as [$^{11}$C]methyl iodide or triflate, as described in for example Solbach et al. Applied Radiation and Isotopes 2005, 62, 591 and Mathis et al. J. Med. Chem. 2003, 46, 2740, or [$^3$H]-methyl iodide, or [$^{14}$C]-methyl iodide.

For example, the compounds of formula Ia, in which one of R1 and R2 is hydroxy (the other is hydrogen), or compounds of formula Ib, in which one of R8 and R11 is hydroxy (the other is hydrogen), or constitute precursors for labeling. When such a precursor is treated with [$^{11}$C]methyl iodide under basic condition, such as in the presence of potassium carbonate, in a solvent such as DMSO, selective O-alkylation occurs in the presence of N-nucleophiles, such as amino or aminomethyl, because of relatively higher reactivity of the oxygen-atom after deprotonation, and thus in the formation of compounds of formula Ia and Ib in which the OH-group has been transformed into the O[$^{11}$C]CH$_3$-group.

Compounds of formula Ib in which R8 or R11 is a protected (e.g. with TBDMS) hydroxy group, $X_8$ is N, and R10 is hydroxy, are useful precursors for labeling through O-alkylation by use of $^{11}$C-methyl iodide in the presence of Ag$_2$CO$_3$ as a base (Shinzo K. Synth Comm 2006, 36, 1235).

The most preferred precursors for labeling by selective introduction of a $^{11}$C-methyl group by N-alkylation, are compounds in which the reactivity to alkylation, of a present competing nucleophilic functional group, such as hydroxy or an aromatic N—H functionality, is lowered or blocked by a suitable protective group. The function of the protective group is, in this context, to protect the nucleophilic functional group from alkylation and should preferably be stable under non-aqueous basic conditions, under which the desired N-alkylation is facilitated, but readily removed by other means after fulfilment of its duty. Such protective groups, and methods for their introduction and removal, are well known to the one skilled in the art. Examples of protective groups useful for protection of aromatic hydroxy-groups against competing alkylation include, but is not limited to, methyl, 2-(trimethylsilyl)ethoxymethyl, alkoxymethyl and t-butyldimethylsilyl. Removal of such a protective group after the alkylation is well known to the one skilled in the art and include, in the case of silyl-based protective groups such as t-butyldimethylsilyl, for example treatment with a fluoride ion source, such as TBAF, or treatment with water under basic conditions in a suitable solvent, such as DMSO in the presence of KOH at rt. Examples of protective groups useful for protection of an aromatic N—H functionality against competing alkylation include, but is not limited to, SO$_2$N(CH$_3$)$_2$, SO$_2$(p-methyl)phenyl, CO$_2$CH$_2$CCl$_3$, CO$_2$(CH$_2$)$_2$Si(CH$_3$)$_2$, t-butyldimethylsilyl and P(=S)phenyl$_2$. In the case where an aromatic hydroxy-functionality, and an aromatic N—H functionality, are simultaneously protected against alkylation, it is preferred to use one protective group, such as t-butyldimethylsilyl, or two different protective groups, which allow simultaneous de-protection of both functionalities in one laboratory step by employment of one de-protection reagent.

Compounds of formula Ia or Ib, carrying an aromatic amino-group, are useful precursor for labeling by initial diazotation (i.e. transformation of the amino-group into the N$_2^+$ moiety), when appropriate, followed by conversion into the corresponding triazine derivative before subsequent treatment with labeled nucleophilic reagents according to standard reactions. Detectable isotopes that may be introduced this way include, but is not limited to $^{18}$F, $^{75}$Br, $^{123}$I, $^{125}$I and $^{131}$I as described in for example Zhu et al. J. Org. Chem. 2002, 67, 943; Maeda et al. J. Label Compd Radiopharm 1985, 22, 487; Berridge et al. J. Label Compd Radiopharm 1985, 22, 687; Suchiro et al. J. Label Compd Radiopharm 1987, 24, 1143; Strouphauer et al. Int. J. Appl. Radiat. Isot. 1984, 35, 787; Kortylevicz et al. J. Label Compd Radiopharm 1994, 34, 1129; Khalaj et al. J. Label Compd Radiopharm 2001, 44, 235 and Rzeczotarski et al. J. Med. Chem. 1984, 27, 156.

In compounds of formula Ib, carrying an aromatic trialkyltin-group, halogenation with labeled reagents results in displacement of the trialkyltin-group as described in for example Staelens et al. J. Label Compd Radiopharm 2005, 48, 101; Hocke et al. Bioorg. Med. Chem. Lett. 2004, 14, 3963; Zhuang et al. J. Med. Chem. 2003, 46, 237; Füchtner et al. Appl. Rad. Isot. 2003, 58, 575 and Kao et al. J. Label Compd Radiopharm 2001, 44, 889. The same precursors are also useful for palladium-catalyzed conversion into the corresponding $^{11}$C-labeled ketones and methyl-derivatives as described in for example Lidström et al. J. Chem. Soc. Perkin Trans. 1 1997, 2701 and Tarkiainen et al. J. Label Compd Radiopharm 2001, 44, 1013. The trialkyltin substituted compounds, in turn, are preferably prepared from the corresponding halides or pseudo-halides, such as the triflates, by well known methods employing palladium as catalyst in reaction with the corresponding distannane. When this methodology is used, the trialkyltin-group is preferably trimethyltin or tributyltin.

Compounds of formula Ib, which are carrying an aromatic trialkyltin group, preferably nBu$_3$Sn, X6 is carbon, X7 or X8 is nitrogen (the other is carbon), and R10 is methylamino, dimethylamino or methoxy, are suitable precursors for labeling with $^{123}$I or $^{125}$I by iododestannylation under oxidative conditions in the presence of labelled iodide according to the method described in, for example, in Zhuang et al. Nucl. Med. Biol. 2001, 28, 887.

When any one of the heterocyclic substituents in a precursor, is a leaving group suitable for nucleophilic aromatic substitution, a labeled nucleophile, such as a halogenide or cyanide, can be introduced by such a displacement resulting in a labeled compound of formula Ia, as described in for example Zhang et al. Appl. Rad. Isot. 2002, 57, 145. The aromatic ring on which the displacement takes place is preferably relatively electron-poor for a facile reaction, and might therefore need to be substituted with an electron-withdrawing activating group such as cyano, carbaldehyde or nitro. Useful reactions, closely related to nucleophilic aromatic substitutions and well known to the one skilled in the art, include the employment of stoichiometric amounts of copper-salts for the introduction of a labeled iodo-atom, and the use of palladium-catalysis for the introduction of a $^{11}C$-labelled cyano-group, as described in for example Musacio et al. J. Label Compd Radiopharm 1997, 34, 39 and Andersson et al. J. Label Compd Radiopharm 1998, 41, 567 respectively. Also, an $^{18}F$-atom may be introduced, for example by use of $K[^{18}F]$-$K_{222}$ in DMSO under microwave irradiation as described in Karramkam, M. et al. J. Labelled Compd. Rad. 2003, 46, 979. If the aromatic ring onto which the leaving group is positioned is more electron-deficient as compared to benzene, such as in 2-halo pyridines and pyrimidines, it is generally not needed to employ activating groups for electrophilic aromatic substitution to take place.

Compounds of formula Ia, where Q is Q2, and Ib, where R3 and R10, respectively, are either of the leaving-groups fluoro, chloro, bromo, iodo, or a sulphonate ester, and either or both of X2 and X4, and X6 and X8 is nitrogen, are suitable precursors for labeling via nucleophilic aromatic substitution. It is furthermore preferable to use a leaving group that is chemically diverse from the group introduced by the reaction with the labeled nucleophile in order to facilitate chromatographic separation of the labeled reaction product from the unconsumed precursor.

Compounds of formula Ib, in which R8 or R11 is a protected (e.g. TBDMS) hydroxy group (the other is hydrogen), and R10 is $O(CH_2)_2OTos$ or $NH(CH_2)_2OTos$, are useful precursors for labeling with fluorine by use of either kryptofix 2.2.2-$[^{18}F]$fluoride complex (Schirrmacher et al. J. Labelled Compd. Rad. 2001, 44, 627), or tetrabutylammonium $[^{18}F]$fluoride in $CH_3CN$ under heating (Hamacher et al. Appl. Radiat. Isotopes 2002, 57, 853), as sources of nucleophilic $^{18}F$ for nucleophilic replacement of the formal leaving group $OTos^-$. Other suitable leaving groups that may be employed are well known to the one skilled in the art and include, but is not limited to bromo, iodo, $OSO_2CF_3$, $OSO_2CH_3$ and $OSO_2phenyl$.

Compounds of formula Ib, in which R8 is H, R11 is OSi $(G3)_3$ or $OCH_2G4$, R10 is $N(CH_3)CHO$, $N(CH_3)COCH_3$, $N(CH_3)CO_2$-t-butyl or $CONH_2$ and R9 is nitro, $N(CH_3)_3^+$, bromo, iodo, chloro are useful precursors for labeling with fluorine by use of kryptofix 2.2.2-$[^{18}F]$fluoride complex as source of nucleophilic $^{18}F$ for nucleophilic replacement of the formal leaving groups R9 (F. Dolle, Curr. Pharm. Design 2005, 11, 3221-3235).

Additional useful methods, well known to the one skilled in the art, for preparation of labeled compounds of formula Ia by functional group transformations of suitable precursors include N-acylation of amines with $[^{11}C]$, $[^{14}C]$, or $[^3H]$acyl chlorides, palladium-catalyzed $[^{11}C]$ or $[^{14}C]$ cyanation of aromatic chlorides, bromides or iodides, transition-metal catalyzed substitution of suitable halides for $^3H$ in the presence of $[^3H]H_2$, and palladium-catalyzed carbonylations with $[^{11/14}C]CO$ (Perry et al. Organometallics 1994, 13, 3346).

COMPOUND EXAMPLES

Below follows a number of non-limiting examples of compounds of the invention. All of the below exemplified compounds, or their corresponding non-labeled analogs, which are not solely precursors and thus indicated to be such, display an $IC_{50}$ of less than 20 µM in the competition binding assay described herein.

General Methods

All solvents used were analytical grade and commercially available anhydrous solvents were routinely used for reactions. Reactions were typically run under an inert atmosphere of nitrogen or argon.

$^1H$ spectra were recorded on a Bruker av400 NMR spectrometer, operating at 400 MHz for proton, equipped with a 3 mm flow injection SEI $^1H/D$-$^{13}C$ probehead with Z-gradients, using a BEST 215 liquid handler for sample injection, or on a Bruker DPX400 NMR spectrometer, operating at 400 MHz for proton, equipped with a 5 mm 4-nucleus probehead equipped with Z-gradients.

Unless specifically noted in the examples, $^1H$ spectra were recorded at 400 MHz in DMSO-$d_6$ as solvent. The residual solvent signal was used as reference. The following reference signals were used: the middle line of DMSO-$d_6$ δ 2.50; the middle line of $CD_3OD$ δ 3.31; $CDCl_3$ δ 7.26. In those instances where spectra were run in a mixture of $CDCl_3$ and $CD_3OD$, the reference was set to 3.31 ppm. All chemical shifts are in ppm on the delta-scale (δ) and the fine splitting of the signals as appearing in the recordings (s: singlet, d: doublet, t: triplet, q: quartet, m: multiplet, br: broad signal), or $^1H$ and $^{13}C$ NMR spectra were recorded at 400 MHz for proton and 100 MHz for carbon-13 on a Varian Mercury Plus 400 NMR Spectrometer equipped with a Varian 400 ATB PFG probe. All deuterated solvents contained typically 0.03% to 0.05% v/v tetramethylsilane, which was used as the reference signal (set at δ 0.00 for both $^1H$ and $^{13}C$).

$^3H$ spectra were recorded on a Bruker DRX600 NMR Spectrometer, operating at 640 MHz for tritium and at 600 MHz for proton, equipped with a 5 mm $^3H/^1H$ SEX probehead with Z-gradients. $^1H$ decoupled $^3H$ spectra were recorded on samples dissolved in $CD_3OD$. For $^3H$ NMR spectra referencing, a ghost reference frequency was used, as calculated by multiplying the frequency of internal TMS in a $^1H$ spectrum with the Larmor frequency ratio between $^3H$ and $^1H$ (1.06663975), according to the description in Al-Rawi et al. J. Chem. Soc. Perkin Trans. II 1974, 1635.

Mass spectra were recorded on a Waters LCMS consisting of an Alliance 2795 or Acquity system (LC), Waters PDA 2996, and ELS detector (Sedex 75) and a ZMD single quadrupole or ZQ mass spectrometer. The mass spectrometer was equipped with an electrospray ion source (ES) operated in a positive or negative ion mode. The capillary voltage was 3 kV and cone voltage was 30 V. The mass spectrometer was scanned between m/z 100-600 with a scan time of 0.7 s. The column temperature was set to 40° C. (Alliance) or 65° C. (Acquity). A linear gradient was applied starting at 100% A (A: 10 mM $NH_4OAc$ in 5% MeCN) and ending at 100% B (B: MeCN). The column used was a X-Terra MS C8, 3.0×50; 3.5 µm (Waters) run at 1.0 mL/min (Alliance), or an Acquity UPLC™ BEH $C_8$ 1.7 µm 2.1×50 mm run at 1.2 mL/min.

Mass spectra (ESMS) were recorded on a Waters MS consisting of an Alliance 2795 (LC) and Waters Micromass ZQ detector at 120° C. The mass spectrometer was equipped with an electrospray ion source (ES) operated in a positive or negative ion mode. The mass spectrometer was scanned between m/z 100-1000 with a scan time of 0.3 s.

Preparative chromatography (prep. HPLC) was run on either of two Waters autopurification HPLCs: (1) equipped with a diode array detector and an XTerra MS C8 column, 19×300 mm, 10 µm. (2) consisting of a ZQ mass spectrometer detector run with ESI in positive mode at a capillary voltage of 3 kV and a cone voltage of 30 V, using mixed triggering, UV and MS signal, to determine the fraction collection. Column: XBridge™ Prep C8 5 µm OBD™ 19×100 mm. Gradients with MeCN/(95:5 0.1M $NH_4OAc$:MeCN) were used at a flow rate of 20 or 25 mL/min.

Microwave heating was performed in a Creator, Initiator or Smith Synthesizer Single-mode microwave cavity producing continuous irradiation at 2450 MHz or microwave heating was performed on a CEM Discover LabMate or on a Biotage Initiator System at the indicated temperature in the recommended microwave tubes.

Precursors

The following examples are useful as precursors for the preparation of radio-labeled compounds of formula Ia and display an $IC_{50}$ of more than 20 μM in the competition binding assay described herein.

5-Methoxybenzofuran boronic acid

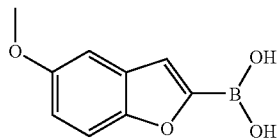

n-Butyllithium 2.5M in hexanes (5.6 mL) was added slowly to a solution of 5-methoxybenzofuran (13.5 mmol) in dry THF (30 mL) at −78° C. After 1 h stirring at −78° C., triisopropylborate (27.0 mmol) was added dropwise and the mixture was stirred for another 20 min at −78° C. The dry ice bath was removed and HCl 2N (aq. 40 mL) was added and the mixture allowed to warm to r.t. and then poured in water (50 mL). The resulting aqueous solution was extracted with ether, the organic layer was washed with brine, dried over $MgSO_4$, filtered and concentrated under vacuum to afford the title compound as a beige powder (2.40 g). $^1$H NMR δ ppm 8.49 (s, 2 H) 7.45 (d, 1 H) 7.38 (s, 1 H) 7.18 (d, 1 H) 6.93 (dd, 1 H) 3.78 (s, 3 H).

5-(5-Methoxy-benzofuran-2-yl)-pyridin-2-ol

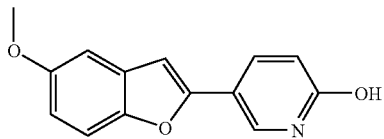

5-methoxybenzofuran boronic acid (230 mg, 1.2 mmol), 5-iodo-2-pyridone (221 mg, 1.0 mmol), Pd(PPh$_3$)$_2$Cl$_2$ (17 mg, 0.024 mmol) and NEt$_3$ (317 μL, 2.4 mmol) were mixed in EtOH (10 mL) in a 20 mL microwave vial. The mixture was stirred at 140° C. for 10 min in a microwave reactor. The solvent was removed under vacuum, water was added and the solution was extracted with EtOAc. The organic layer was dried over Na2SO4, filtered and the solvent removed under vacuum. The crude substance was purified by preparative HPLC to afford the title compound as a white solid (20 mg). $^1$H NMR δ ppm 11.95 (br. s., 1 H) 7.94 (dd, 1 H) 7.88 (s, 1 H) 7.44 (d, 1 H) 7.00-7.20 (m, 2 H) 6.84 (dd, 1 H) 6.48 (d, 1H) 3.78 (s, 3 H); MS m/z 242 (M+H).

Compounds

Below follows a number of non-limiting examples of compounds of the invention. All of the below exemplified compounds, or their corresponding non-labeled analogs, which are not solely precursors and thus indicated to be such, display an $IC_{50}$ of less than 20 μM in the competition binding assay described herein.

Example 1

5-(5-Methoxy-benzofuran-2-yl)-pyridine-2-carboxylic acid amide

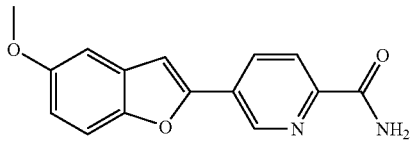

5-methoxybenzofuran boronic acid (1.2 mmol), 5-bromopyridine-2-carboxamide (1.0 mmol), Pd(PPh$_3$)$_2$Cl$_2$ (0.024 mmol) and NEt$_3$ (317 μL) were mixed in EtOH (10 mL) in a 20 mL microwave vial. The mixture was stirred at 140° C. for 10 min in a microwave reactor, filtered, and the precipitate was washed with water and EtOAc and dried under vacuum to afford the title compound (75 mg). $^1$H NMR δ ppm 9.10 (d, 1 H) 8.34 (dd, 1 H) 8.21 (br. s., 1 H) 8.00 (d, 1 H) 7.52-7.72 (m, 3 H) 7.25 (d, 1 H) 7.00 (dd, 1 H) 3.82 (s, 3H); MS m/z 269 (M+H).

Example 2

5-(5-Hydroxy-benzofuran-2-yl)-pyridine-2-carboxylic acid amide

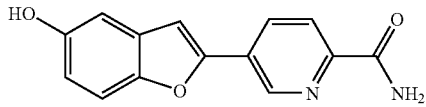

5-(5-Methoxy-benzofuran-2-yl)-pyridine-2-carboxylic acid amide (0.21 mmol) was mixed with CH$_2$Cl$_2$ (3 mL) at 0° C. under argon atmosphere. BBr$_3$ (1M in CH$_2$Cl$_2$) (1.0 mL) was added dropwise and the mixture was stirred for 2 h at rt. The mixture was hydrolysed with H$_2$O followed by NaHCO$_3$ (sat. aq.). The resulting mixture was filtered, and the obtained precipitate was washed with H$_2$O and EtOAc. The solid was dried at 40° C. for 15 h under vacuum to give the title compound (20 mg). $^1$H NMR δ ppm 9.08 (d, 1 H) 8.33 (dd, 1 H) 8.20 (br. s., 1 H) 7.97 (d, 1 H) 7.61 (br. s., 1 H) 7.54 (s, 1 H) 7.47 (d, 1 H) 7.02 (d, 1 H) 6.85 (none, 1 H); MS m/z 255 (M+H).

Example 3

6-(5-Methoxy-benzofuran-2-yl)-nicotinamide

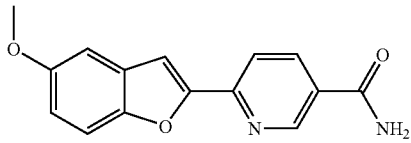

5-methoxybenzofuran boronic acid (1.2 mmol), 6-bromonicotinamide (1.0 mmol), Pd(PPh$_3$)$_2$Cl$_2$ (0.024 mmol) and NEt$_3$ (317 μL) were mixed in EtOH (10 mL) in a 20 mL microwave vial. The mixture was stirred at 140° C. for 10 min in a microwave reactor. The mixture was filtered, the obtained precipitate was washed with water and EtOAc and dried under vacuum to afford the title compound (85 mg). $^1$H NMR δ ppm 9.14 (d, 1 H) 8.42 (dd, 1 H) 7.97-8.25 (m, 2 H)

7.63-7.80 (m, 2 H) 7.58 (d, 1 H) 7.22 (d, 1 H) 6.98 (dd, 1H) 3.81 (s, 3 H); MS m/z 269 (M+H).

Example 4

6-(5-Hydroxy-benzofuran-2-yl)-nicotinamide

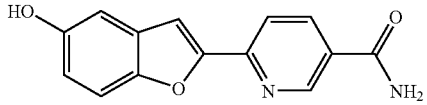

6-(5-Methoxy-benzofuran-2-yl)-nicotinamide (0.25 mmol) was mixed with CH$_2$Cl$_2$ (3 mL) at 0° C. under argon atmosphere. BBr$_3$ (1M in CH$_2$Cl$_2$) (1.0 mL) was added dropwise and the mixture was stirred for 2 h at rt. The mixture was hydrolysed with H$_2$O followed by NaHCO$_3$ (sat. aq.). The resulting mixture was filtered, and the obtained precipitate was washed with H$_2$O and EtOAc. The solid was dried at 40° C. for 15 h under vacuum (12 mg).
$^1$H NMR δ ppm 9.11 (d, 1 H) 8.38 (dd, 1 H) 8.01-8.23 (m, 2 H) 7.63-7.76 (m, 1 H) 7.59 (s, 1 H) 7.46 (d, 1 H) 7.00 (d, 1 H) 6.83 (dd, 1 H); MS m/z 256 (M+H).

Example 5

[5-(5-Methoxy-benzofuran-2-yl)-pyridin-2-yl]-methylamine

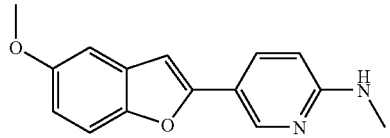

5-methoxybenzofuran boronic acid (1.2 mmol), 5-bromopyridine-2-methylamine (1.0 mmol), Pd(PPh$_3$)$_2$Cl$_2$ (0.024 mmol) and NEt$_3$ (317 µL) were mixed in EtOH (10 mL) in a 20 mL microwave vial. The mixture was stirred at 140° C. for 10 min in a microwave reactor. The solvent was removed under vacuum, water was added and the solution was extracted with EtOAc. The organic layer was dried over Na$_2$SO$_4$, filtered and concentrated under vacuum. The crude substance was purified by preparative HPLC to afford the title compound as a white solid (100 mg). $^1$H NMR δ ppm 8.53 (d, 1 H) 7.84 (dd, 1 H) 7.44 (d, 1 H) 7.08 (d, 1 H) 7.04 (s, 1 H) 6.91 (d, 1 H) 6.81 (dd, 1 H) 6.55 (d, 1 H) 3.78 (s, 3 H) 2.83 (d, 3 H); MS m/z 255 (M+H).

Example 6

2-(6-Methylamino-pyridin-3-yl)-benzofuran-5-ol

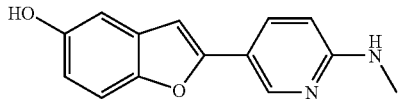

[5-(5-Methoxy-benzofuran-2-yl)-pyridin-2-yl]-methylamine (0.24 mmol) was mixed with CH$_2$Cl$_2$ (3 mL) at 0° C. under argon atmosphere. BBr$_3$ (1M in CH$_2$Cl$_2$) (1.0 mL, 1.0 mmol) was added dropwise and the mixture was stirred for 2 h at rt. The mixture was hydrolysed with H$_2$O followed by NaHCO$_3$ (sat. aq.) solution. The resulting mixture was extracted with EtOAc and the organic extracts were dried over Na$_2$SO$_4$. After filtration and evaporation of the solvent, the crude material was purified by preparative HPLC to afford the title compound as a white solid (21 mg). $^1$H NMR δ ppm 9.10 (s, 1 H) 8.50 (d, 1 H) 7.81 (dd, 1 H) 7.32 (d, 1 H) 6.96 (s, 1 H) 6.81-6.94 (m, 2 H) 6.66 (dd, 1 H) 6.54 (d, 1 H) 2.82 (d, 3 H); MS m/z 241 (M+H).

Example 7

6-(5-Methoxy-benzofuran-2-yl)-pyridazin-3-ylamine

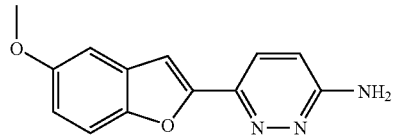

5-methoxybenzofuran boronic acid 1.2 mmol), 6-bromo-3-pyridazinamine (1.0 mmol), Pd(PPh$_3$)$_2$Cl$_2$ (0.024 mmol) and NEt$_3$ (317 µL) were mixed in EtOH (10 mL) in a 20 mL microwave vial. The mixture was stirred at 140° C. for 10 min in a microwave reactor. The solvent was removed under vacuum, water was added and the solution was extracted with EtOAc. The organic layer was dried over Na$_2$SO$_4$, filtered and the solvent removed under vacuum. The crude substance was purified by preparative HPLC to afford the title compound as a white solid (51 mg). $^1$H NMR δ ppm 7.77 (d, 1 H) 7.52 (d, 1 H) 7.35 (s, 1H) 7.19 (d, 1 H) 6.79-6.98 (m, 2 H) 6.72 (s, 2 H) 3.80 (s, 3 H); MS m/z 242 (M+H).

Example 8

2-(6-Amino-pyridazin-3-yl)-benzofuran-5-ol

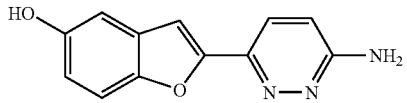

6-(5-Methoxy-benzofuran-2-yl)-pyridazin-3-ylamine (0.14 mmol) was mixed with CH$_2$Cl$_2$ (3 mL) at 0° C. under argon atmosphere. BBr$_3$ (1M in CH$_2$Cl$_2$, 1.0 mL) was added dropwise and the mixture was stirred for 2 h at rt. The mixture was hydrolysed with H$_2$O followed by NaHCO$_3$ (sat. aq.). The resulting mixture was extracted with EtOAc and the organic extracts were dried over Na$_2$SO$_4$. After filtration and evaporation of the solvent, the crude material was purified by preparative HPLC to afford the title compound as a yellow solid (8 mg). $^1$H NMR δ ppm 9.21 (s, 1 H) 7.74 (d, 1 H) 7.40 (d, 1 H) 7.27 (s, 1 H) 6.96 (d, 1 H) 6.86 (d, 1 H) 6.76 (dd, 1 H) 6.69 (s, 2 H); MS m/z 228 (M+H).

Example 9

5-(1-benzothien-2-yl)pyridine-2-carboxamide

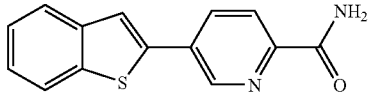

2-Benzothienylboronic acid (1.8 mmol), 5-bromopyridine-2-carboxamide (1.2 mmol), 2M K$_2$CO$_3$ (2.4 mL), Pd(dppf)Cl$_2$ (0.12 mmol) were mixed and stirred at 80° C. in DMF for 3 h. The reaction mixture was filtered and to the filtrated was added EtOAc and H$_2$O. The layers were separated and the aqueous phase was extracted twice with EtOAc. The organic extracts were dried over Na$_2$SO$_4$. The solvent was evaporated in vacuo to give a brown solid. The crude was subjected to reverse phase HPLC to afford the title compound as a light brown solid (11 mg). ¹H NMR δ ppm 9.07 (d, 1 H) 8.34 (dd, 1 H) 8.24-8.02 (m, 5 H) 7.73 (s br, 1 H) 7.54-7.37 (m, 2 H); MS m/z 255 (M+H).

Example 10

5-(1-Benzofuran-2-yl)pyridine-2-carboxamide

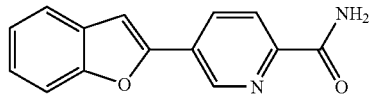

2-Benzofuranboronic acid (3.1 mmol), 5-bromopyridine-2-carboxamide (3.7 mmol), 2M K₂CO₃ (aq., 6 mL) and Pd(dppf)Cl₂ (0.31 mmol) were mixed and stirred at 80° C. in DMF for 2 h. The reaction mixture was filtered and washed with H₂O and EtOAc. DMSO was added to the solid remains and filtered. The filtrate was collected and purified by reverse phase HPLC to afford the title compound as a white solid (2.5 mg). ¹H NMR δ ppm 9.18 (d, 1 H) 8.46 (dd, 1 H) 8.13-8.19 (m, 2 H) 7.68-7.78 (m, 4 H) 7.43-7.30 (m, 2 H); MS m/z 239 (M+H).

Example 11

2-(1-benzofuran-2-yl)-6-methoxyimidazo[1,2-a]pyridine

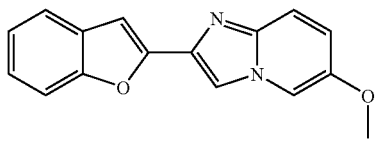

Benzofuran boronic acid (0.289 mmol), 2-bromo-6-methoxyimidazo[1,2-a]pyridine (0.263 mmol), Pd(dppf)Cl₂ (0.013 mmol) and K₂CO₃ (aq.) were stirred in DMF at 80° C. under argon for 1 h. The reaction mixture was allowed to cool to r.t. and brine was added. The reaction mixture was extracted with CH₂Cl₂ and the organic phase was filtered. The solvents were removed under reduced pressure and the residue purified by reverse phase HPLC to afford the title compound (0.5 mg). ¹H NMR δ ppm 7.95 (s, 1 H) 7.67 (d, 1 H) 7.65-7.60 (m, 1 H) 7.58-7.51 (m, 2 H) 7.33-7.20 (m, 3 H) 7.03 (dd, 1 H) 3.86 (s, 3 H); MS m/z 265 (M+H).

Example 12

2-(6-Fluoro-5-methylamino-pyridin-2-yl)-benzofuran-5-ol

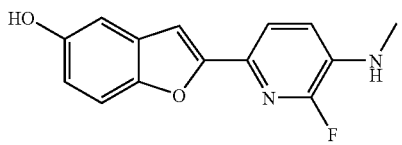

a) 6-Bromo-2-fluoro-pyridin-3-ylamine

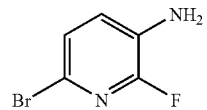

To a stirred solution of 2-fluoro-pyridin-3-ylamine (3.0 g, 26.79 mmol) in acetic acid (24 mL), sodium acetate (2.17 g, 26.46 mmol) was added. The reaction mixture was cooled to 0-5° C. and a solution of bromine (1.37 mL, 26.74 mmol) in acetic acid (8 ml) was added dropwise. After 1 hour the reaction mixture was cooled to 0° C., 10% aqueous sodium hydroxide solution was added to adjust the pH ~5 and the product was extracted with ethyl acetate (200 mL). The organic layer was washed with water, brine, dried over magnesium sulfate and concentrated under reduced pressure. The crude product was purified by flash column chromatography using 20% ethyl acetate in hexane to afford 6-bromo-2-fluoro-pyridin-3-ylamine (3.9 g) as a brown solid. ¹H NMR (400 MHz, CDCl₃) δ: 7.15 (d, J=7.8 Hz, 1H), 7.00 (dd, J=10.1, 7.8 Hz, 1H), 3.80 (s, 2H). ESMS: m/z 191.32, 193.34 [M+1]⁺ b) 2-Fluoro-6-(5-methoxy-benzofuran-2-yl)-pyridin-3-ylamine

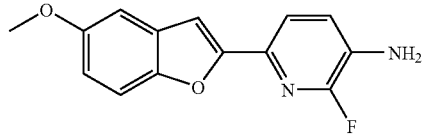

5-Methoxybenzofuran boronic acid (345 mg, 1.80 mmol), 6-bromo-2-fluoro-pyridin-3-ylamine (286.5 mg, 1.50 mmol), Pd(PPh₃)₂Cl₂ (25.2 mg, 0.036 mmol) and Et₃N (475.5 μL, 3.41 mmol) were mixed in EtOH (10 mL) in a microwave vial. The reaction mixture was stirred at 140° C. for 10 minutes in a microwave reactor. The volatiles were then removed under reduced pressure and water was added (20 mL). The product was extracted with ethyl acetate (30 mL). The organic layer was dried over Na₂SO₄ and concentrated in vacuo. Purification of the crude product by flash column chromatography using 25% ethyl acetate in hexane gave 2-fluoro-6-(5-methoxy-benzofuran-2-yl)-pyridin-3-ylamine (268 mg) as an off-white solid. ¹H NMR (400 MHz, CDCl₃) δ: 7.58 (d, J=7.6 Hz, 1 H), 7.39 (d, J=9.0 Hz, 1H), 7.15 (m, 1H), 7.14 (s, 1H), 7.04 (d, J=2.6 Hz, 1H), 6.88 (m, 1H), 3.95 (s, 2H), 3.85 (s, 3H). ESMS: m/z 259.47 [M+1]⁺ c) [2-Fluoro-6-(5-methoxy-benzofuran-2-yl)-pyridin-3-yl]-methyl-amine

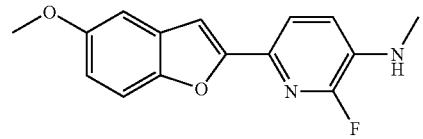

To a stirred solution of 2-fluoro-6-(5-methoxy-benzofuran-2-yl)-pyridin-3-ylamine (97 mg, 0.376 mmol) in a mixture of MeOH (2 mL) and dichloroethane (1 mL), formaldehyde (37% solution in water, 0.167 mL, 2.23 mmol) and acetic acid (50 μL, 0.87 mmol) were added. The reaction mixture was stirred for 2 hours at room temperature, then NaCNBH₃ (94 mg, 1.50 mmol) was added in one portion and the stirring was continued for 45 minutes. The reaction was then quenched by addition of water (2 mL). The volatiles were removed under reduced pressure and the residue was extracted with dichloromethane (50 mL). The organic layer was washed with water, dried over Na₂SO₄, filtered and concentrated. The product was purified by flash column chromatography using 20% ethyl acetate in hexane to afford [2-fluoro-6-(5-methoxy-benzofuran-2-yl)-pyridin-3-yl]-methyl-amine (35.7 mg) as an off-white solid. ¹H NMR (400 MHz, CDCl₃) δ: 7.64 (d, J=8.2 Hz, 1H), 7.38 (d, J=8.98 Hz, 1H), 7.09 (s, 1H), 7.03 (d, J=2.34 Hz, 1H), 6.99 (dd, J=10.15, 8.20 Hz, 1H), 6.87 (dd, J=8.78, 2.54 Hz, 1H), 4.21 (br. s, 1H), 3.85 (s, 3H), 2.94 (d, J=5.07 Hz, 3H)

d) 2-(6-Fluoro-5-methylamino-pyridin-2-yl)-benzofuran-5-ol

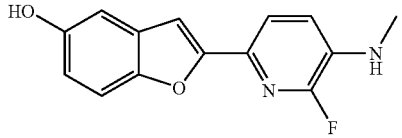

To a stirred solution of [2-fluoro-6-(5-methoxy-benzofuran-2-yl)-pyridin-3-yl]-methyl-amine (31 mg, 0.114 mmol) in dichloromethane (3 mL) at 0° C. under nitrogen atmosphere, BBr₃ (1M solution in CH₂Cl₂, 0.568 mL, 0.568 mmol) was added dropwise. The reaction mixture was stirred for 1.5 hours at room temperature. The mixture was then cooled to 0° C., saturated sodium bicarbonate solution was added (5 mL) and the resulting mixture was extracted with dichloromethane (50 mL). The organic layer was washed with brine, dried over Na₂SO₄ and concentrated under reduced pressure. Purification of the crude product by flash chromatography using 30% ethyl acetate in hexane afforded the title compound 2-(6-fluoro-5-methylamino-pyridin-2-yl)-benzofuran-5-ol (22 mg) as an off-white solid. ¹H NMR (400 MHz, METHANOL-d₄) δ: 7.62 (d, J=7.90 Hz, 1H), 7.28 (d, J=8.78 Hz, 1H), 7.08 (dd, J=10.54, 8.20 Hz, 1H), 6.97 (s, 1H), 6.92 (d, J=2.34 Hz, 1H), 6.74 (dd, J=8.78, 2.34 Hz, 1H), 2.87 (s, 3H). ESMS: m/z 259.47 [M+1]⁺

Example 13

2-(2-Fluoro-6-methylamino-pyridin-3-yl)-benzofuran-5-ol

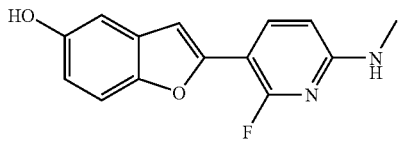

a) 5-Bromo-6-fluoro-pyridin-2-ylamine

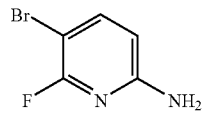

To a stirred solution of 6-fluoro-pyridin-2-ylamin (1.0 g, 8.93 mmol) in acetonitrile (50 mL), protected from light and under nitrogen atmosphere, N-bromosuccinimide (0.79 g, 4.46 mmol) was added. After 1 hour, an additional portion of N-bromosuccinimide (0.79 g, 4.46 mmol) was added and the stirring was continued for 3 hours. The volatiles were removed under reduced pressure and the crude material was purified by flash column chromatography using a gradient of 25% to 30% ethyl acetate in hexane to give 5-bromo-6-fluoro-pyridin-2-ylamine (1.45 g) as a white solid. ¹H NMR (400 MHz, CHLOROFORM-d) δ: 7.60 (t, J=8.59 Hz, 1 H) 6.15-6.36 (m, 1 H) 4.58 (br. s., 2 H)
ESMS: m/z 193.34 [M+1]⁺ for ⁸¹Br isotope b) 6-Fluoro-5-(5-methoxy-benzofuran-2-yl)-pyridin-2-ylamine

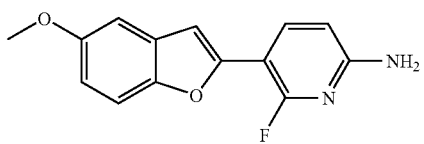

5-Methoxybenzofuran boronic acid (230 mg, 1.20 mmol), 5-bromo-6-fluoro-pyridin-2-ylamine (191 mg, 1.00 mmol), Pd(PPh₃)₂Cl₂ (16.8 mg, 0.024 mmol) and Et₃N (317 μL, 2.27 mmol) were mixed in EtOH (10 mL) in a microwave vial. The reaction mixture was stirred at 140° C. for 15 minutes in a microwave reactor. The volatiles were then removed under reduced pressure, the residue was suspended in water and the product was extracted with ethyl acetate. The organic layer was dried over Na₂SO₄, filtered and concentrated in vacuo. Purification of the crude product by flash column chromatography using 25% ethyl acetate in hexane gave 6-fluoro-5-(5-methoxy-benzofuran-2-yl)-pyridin-2-ylamine (130 mg) as an off-white solid. ¹H NMR (400 MHz, CHLOROFORM-d) δ: 8.05-8.21 (m, 1 H) 7.36 (d, J=8.59 Hz, 1 H) 7.03 (d, J=1.95 Hz, 1 H) 6.97 (d, J=3.12 Hz, 1 H) 6.86 (dd, J=8.78, 2.54 Hz, 1 H) 6.45 (d, J=6.63 Hz, 1 H) 4.66 (br. s., 2 H) 3.86 (s, 3 H)

c) [6-Fluoro-5-(5-methoxy-benzofuran-2-yl)-pyridin-2-yl]-carbamic acid tert-butyl ester

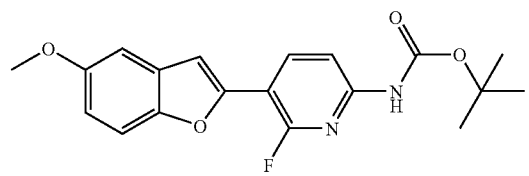

To a stirred solution of 6-fluoro-5-(5-methoxy-benzofuran-2-yl)-pyridin-2-ylamine (220 mg, 0.853 mmol) in THF (10 mL) at 0° C. NaHMDS (1.02 mL. 1.02 mmol, 1M solution in THF) was added and stirred for 15 minutes. This was followed by addition of di-tert-butyl dicarbonate (262 mg, 1.2 mmol) in THF (5 mL) over a period of 5 minutes. The reaction mixture was stirred for 2 hours at room temperature. EtOAc and saturated aqueous NaHCO₃ were added and the layers were separated. The organic layer was washed with brine, dried over Na₂SO₄, filtered, and concentrated under reduced pressure. The crude product was purified by flash column chromatography using 10% ethyl acetate in hexane to give title compound (81 mg) as an off-white solid. ¹H NMR (400 MHz, CHLOROFORM-d) δ: 8.31-8.38 (m, 1 H) 7.93 (dd, J=8.60, 1.56 Hz, 1 H) 7.41 (d, J=8.99 Hz, 1 H) 7.16 (s, 1 H) 7.10 (d, J=3.52 Hz, 1 H) 7.06 (d, J=2.74 Hz, 1 H) 6.92 (dd, J=8.99, 2.74 Hz, 1 H) 3.87 (s, 3 H) 1.55 (s, 9 H)

d) [6-Fluoro-5-(5-methoxy-benzofuran-2-yl)-pyridin-2-yl]-methyl-carbamic acid tert-butyl ester

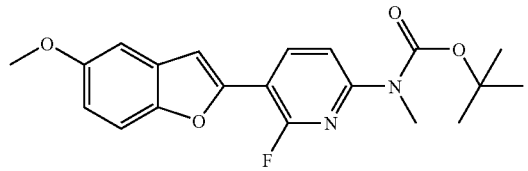

To a stirred solution of [6-fluoro-5-(5-methoxy-benzofuran-2-yl)-pyridin-2-yl]-carbamic acid tert-butyl ester (78 mg, 0.218 mmol) in DMF (5 mL) at 0° C., NaH (11 mg, 0.26 mmol, 57% dispersion in oil) was added and the resulting mixture was stirred for 10 minutes. Methyl iodide (15 μL, 0.24 mmol) was then added and the stirring was continued for 30 minutes at room temperature. Additional portions of NaH (11 mg, 0.26 mmol, 57% dispersion in oil) and methyl iodide (15 μL, 0.24 mmol) were added and the solution was stirred for 1 hour. The reaction mixture was quenched with water (5 mL) and the product was extracted with ethyl acetate. The organic layer was washed with brine, dried over $Na_2SO_4$, filtered and concentrated. Purification of the crude product by flash column chromatography using 10% ethyl acetate in hexane afforded title compound (66 mg) as an off-white solid. $^1$H NMR (400 MHz, CHLOROFORM-d) δ: 8.25-8.33 (m, 1 H) 7.87 (m 1H) 7.41 (d, J=9.37 Hz, 1 H) 7.14 (s, 1 H) 7.06 (d, J=2.34 Hz, 1 H) 6.92 (d, J=8.98 Hz, 1 H) 3.86 (s, 3 H) 3.43 (s, 3 H) 1.56 (s, 9 H)

e) 2-(2-Fluoro-6-methylamino-pyridin-3-yl)-benzofuran-5-ol

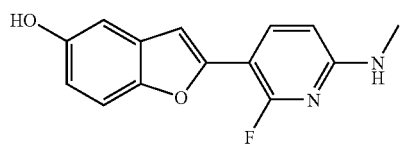

To a stirred solution of [6-fluoro-5-(5-methoxy-benzofuran-2-yl)-pyridin-2-yl]-methyl-carbamic acid tert-butyl ester (66 mg, 0.184 mmol) in dichloromethane (30 mL) at 0° C. under nitrogen atmosphere, $BBr_3$ (1M solution in $CH_2Cl_2$, 0.92 mL, 0.92 mmol) was added dropwise. The reaction mixture was stirred at room temperature overnight and then cooled to 0° C. Saturated sodium bicarbonate solution was added and the resulting mixture was extracted subsequently with 5% methanol in dichloromethane and with 5% methanol in ethyl acetate. The organic layers were washed with brine separately, dried over $Na_2SO_4$, filtered, concentrated and flash chromatographed using 30% ethyl acetate in hexane to give) 2-(2-fluoro-6-methylamino-pyridin-3-yl)-benzofuran-5-ol (19.9 mg) as a off white solid. $^1$H NMR (400 MHz, METHANOL-$d_4$) δ: 8.02 (m, 1H), 7.27 (d, J=8.59 Hz, 1H), 6.90 (d, J=2.34 Hz, 1H), 6.77 (d, J=3.51 Hz, 1H), 6.70 (dd, J=8.59, 2.34 Hz, 1H), 6.43 (dd, J=8.59, 1.95 Hz, 1H), 2.89 (s, 3H). ESMS: m/z 259.47 [M+1]$^+$ Example 14

2-(5-fluoro-6-methylamino-pyridin-3-yl)-benzofuran-5-ol

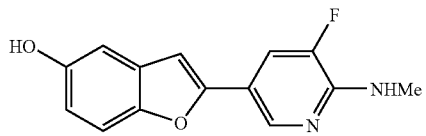

a) 5-Bromo-3-fluoro-pyridin-2-ylamine

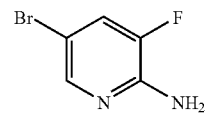

To a solution of 3-fluoro-pyridin-2-ylamine (1.0 g, 8.92 mmol) in 300 mL of acetonitrile, NBS (794 mg, 4.46 mmol) was added at 0° C. The reaction mixture was stirred vigorously for 15 minutes (protected from light) at 0° C. and then at room temperature for 1 hour. The additional portion of NBS (794 mg, 4.46 mmol) was added at 0° C. and the solution was stirred at room temperature for 2 hours. The reaction mixture was quenched by addition $Na_2S_2O_3$ (saturated aqueous solution, 40 mL) and the product was extracted with EtOAc (3×40 mL). The combined organic extracts were washed with brine (2×50 mL), dried over $MgSO_4$ and concentrated in vacuo. The obtained crude yellowish solid was purified by Biotage using 3-20% EtOAc in hexane to afford 5-bromo-3-fluoro-pyridin-2-ylamine (1.2 g). $^1$H NMR (400 MHz, CHLOROFORM-d) δ ppm 7.93 (d, J=1.56 Hz, 1 H) 7.37 (dd, J=9.76, 1.95 Hz, 1 H) 4.63 (br. s., 2 H)

b) (5-Bromo-3-fluoro-pyridin-2-yl)-carbamic acid tert-butyl ester

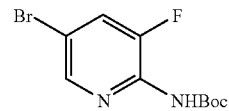

To a solution of 5-bromo-3-fluoro-pyridin-2-ylamine (1.2 g, 6.28 mmol) in THF (100 mL) was added NaHMDS (1M in THF, 6.2 mL) at 0° C. The solution was stirred vigorously for 15 minutes (turned green). $Boc_2O$ (1.3 g, 5.95 mmol) dissolved in THF (5 mL) was added to the reaction mixture slowly over 30 minutes at 0° C. The reaction mixture was then warmed to room temperature, stirred for 5 hours and was quenched with $NaHCO_3$ (saturated aqueous solution, 40 mL). The product was extracted with EtOAc (3×40 mL). The organic extracts were dried over $MgSO_4$ and concentrated in vacuo. The residue was purified by Biotage using 3-10% EtOAc in hexane to give title compound (600 mg) as a white solid. $^1$H NMR (400 MHz, CHLOROFORM-d) δ ppm 8.29 (br. s, 1 H) 7.58 (dd, J=9.37, 1.95 Hz, 1 H) 6.89 (br. s., 1 H) 1.53 (s, 9 H)

c) (5-Bromo-3-fluoro-pyridin-2-yl)-methyl-carbamic acid tert-butyl ester

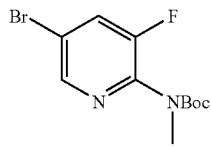

To a solution of (5-bromo-3-fluoro-pyridin-2-yl)-carbamic acid tert-butyl ester (600 mg, 2.06 mmol) in dry DMF (20 mL), NaH (130 mg, 3.08 mmol) was added at 0° C. The solution was stirred vigorously for 10 minutes at 0° C. and MeI (180 µL, 2.88 mmol) was added. After 30 minutes, the reaction mixture was quenched with $NH_4Cl$ (saturated aqueous solution) and the product was extracted with EtOAc (3×40 mL). The combined organic extracts were washed with water, dried over $MgSO_4$ and concentrated in vacuo. The residue was purified by Biotage using 3-15% EtOAc in hexane to afford title compound (470 mg) as a white solid. $^1$H NMR (400 MHz, CHLOROFORM-d) δ ppm 8.23 (d, J=1.95 Hz, 1 H) 7.52 (dd, J=8.59, 1.95 Hz, 1 H) 3.22 (s, 3 H) 1.37 (s, 9 H)

d) [3-Fluoro-5-(5-methoxy-benzofuran-2-yl)-pyridin-2-yl]-methyl-carbamic acid tert-butyl ester

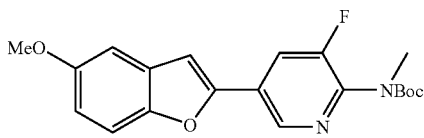

To a degassed solution of (5-bromo-3-fluoro-pyridin-2-yl)-methyl-carbamic acid tert-butyl ester (310 mg, 1.01 mmol) in EtOH (10 mL) were added $Pd(PPh_3)_2Cl_2$ (142 mg, 0.20 mmol), bezofuran boronic acid (291 mg, 1.52 mmol) and $Et_3N$ (283 µL, 2.03 mmol). The reaction was stirred in a microwave reactor for 30 minutes at 100° C. The volatiles were removed under reduced pressure and the residue was purified by flash column chromatography using 10% EtOAc in hexane to obtain title compound (130 mg) as a white solid. $^1$H NMR (400 MHz, CHLOROFORM-d) δ ppm 8.68 (br. s, 1 H) 7.80 (d, J=11.71 Hz, 1 H) 7.42 (d, J=8.98 Hz, 1 H) 7.04 (s, 2 H) 6.93 (dd, J=8.98, 2.34 Hz, 1 H) 3.85 (s, 3H) 3.35 (s, 3 H) 1.46 (s, 9 H). ESMS: m/z 359.41 (M+1)

e) 2-(5-Fluoro-6-methylamino-pyridin-3-yl)-benzofuran-5-ol

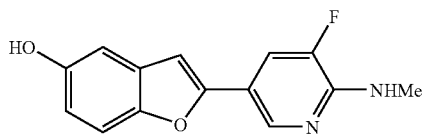

To a solution of [3-fluoro-5-(5-methoxy-benzofuran-2-yl)-pyridin-2-yl]-methyl-carbamic acid tert-butyl ester (130 mg, 0.35 mmol) in dry $CH_2Cl_2$ (400 mL), $BBr_3$ (2.1 mL, 2.10 mmol) was added at −78° C. The reaction mixture was allowed to warm to room temperature and the stirring was continued for 14 hours. The reaction was then quenched by addition of saturated aqueous $NaHCO_3$ and the product was extracted with EtOAc (3×30 mL). The combined extracts were dried over $MgSO_4$ and concentrated in vacuo. The crude residue was purified by preparative TLC using 30% EtOAc in $CH_2Cl_2$ to afford 2-(5-fluoro-6-methylamino-pyridin-3-yl)-benzofuran-5-ol (37 mg) as a white solid.

$^1$H NMR (400 MHz, METHANOL-$d_4$) δ ppm 8.31 (br. s, 1 H) 7.68 (dd, J=12.10, 1.95 Hz, 1 H) 7.29 (d, J=8.59 Hz, 1 H) 6.86-6.94 (m, 2 H) 6.72 (dd, J=8.78, 2.54 Hz, 1 H) 2.99 (s, 3 H). ESMS: m/z 259.41 (M+1)

Biological Examples

The following compounds were used as comparative compounds and are referred to in the text below by their indicated corresponding names.

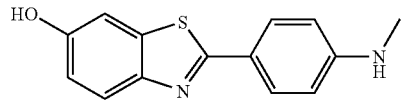

PIB

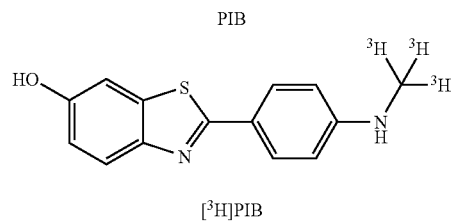

[$^3$H]PIB

Compounds of the present invention were tested in one or several of the following assays/experiments/studies:

Competition Binding Assay

Competition binding was performed in 384-well FB filter plates using synthetic Aβ 1-40 in 2.7 nM of [$^3$H]PIB (or another $^3$H-labeled radioligand when so mentioned) in phosphate buffer at pH 7.5, by adding various concentrations of non-radioactive compounds originally dissolved in DMSO. The binding mixture was incubated for 30 min at room temperature, followed by vacuum filtration, and subsequentially by washing twice with 1% Triton-X100. Scintillation fluid was thereafter added to the collected Aβ 1-40 on the filter plate, and the activity of the bound remaining radioligand ([$^3$H]PIB or another $^3$H-labeled radioligand) was measured using 1450 Microbeta from PerkinElmer.

Dissociation Experiments

Dissociation experiments were performed in 96-well polypropylene deep well plates. 2 µM human synthetic Aβ 1-40 fibrils in phosphate buffer pH 7.5, or buffer alone as control, was incubated with 9 nM of a $^3$H-labeled radioligand of the present invention for 4 h at room temperature. Dissociation was started at different time points, by the addition of an equal volume of a non-labeled compound of the present invention, or a reference compound (10 EM), in 4% DMSO in phosphate buffer at pH 7.5. The radioactivity still bound to the Aβ 1-40 fibrils at the end of the incubation was detected on FB filters after filtration in a Brandel apparatus using a wash buffer containing 0.1% Triton-X100.

In vivo Rat Brain Entry Studies

Brain exposure after i.v administration was determined in rat brains using cassette dosing. Four different compounds were dosed followed by plasma and brain sampling at 2 and 30 minutes after the dosing. 2 to 30 min brain concentration ratios, and percentage of total of injected dose after 2 mins found in brain, were calculated. The compound concentrations were determined by analysis of protein precipitated plasma samples by reversed-phase liquid chromatography coupled to a electrospray tandem mass spectrometer.

Binding to Amyloid Plaques in Post-mortem Human AD Brains and Transgenic Mice Brains Slide-mounted brain sections (10 μm) from APP/PS1 transgenic mice were collected at the level of the lateral septum (bregma+0.98 mm; see Paxinos and Franklin, 2001). Human cortical sections (7 μm) from two AD patients and 1 control subject were obtained from a Dutch tissue bank.

Sections were preincubated for 30 minutes at room temperature in 50 mM Tris HCl (pH 7.4) in the presence or absence of 1 μM PIB. Sections were transferred to buffer containing tritium-labeled compound (1 nM) with or without PIB (1 μM) and incubated for 30 minutes at room temperature. Incubation was terminated by 3 consecutive 10 minute rinses in buffer (1° C.) followed by a rapid rinse in distilled water (1° C.). Sections were air dried in front of a fan. Dried sections and plastic tritium standards (Amersham microscales-$^3$H) were apposed to phosphoimage plates (Fuji) in a cassette and exposed overnight. The following morning, the image plates were processed with a Fuji phosphoimager (BAS 2500) using BAS Reader software. The resulting image was converted to TIF format using Aida software, optimized with Adobe Photoshop (v 8.0) and quantified using Image-J (NIH). Data were statistically analyzed using Excel.

Binding in APP/PS1 Mouse Brain after Compound Administration in-vivo

Naïve, awake mice were restrained and intravenously infused via the tail vein with either a tritium labeled compound of the present invention, or a tritium labeled reference compound via the tail vein. In one type of experiment, the animals were rapidly anesthetized with isofluorane and decapitated twenty minutes after compound administration (1 mCi). In another type of experiment, mice were given 1 mCi of a compound and were anesthetized and decapitated at a timepoint of 20, 40 or 80 minutes after administration. Brains were removed and frozen with powdered dry ice. Brains were sectioned (10 μm) in the coronal plane at the level of the striatum with a cryostat, thaw-mounted onto superfrost microscope slides and air-dried.

Methods designed to optimize the imaging of bound ligand after in vivo administration were thereafter employed. To selectively reduce unbound radioactivity levels, one-half of the sections were rinsed (3×10 minutes) in cold (1° C.) Tris buffer (50 mM, pH7.4) followed by a rapid rinse in cold (1° C.) deionized water. Sections were then air dried in front of a fan. Rinsed as well as unrinsed sections and tritium standards were exposed to phosphoimage plates (Fuji). Phosphoimage plates were processed with a Fujifilm BAS-2500 phosphoimager using BAS Reader software.

Biological Example 1

Characterization of Specific Binding of Novel 2-heteroaryl Substituted Benzothiophene and Benzofurane Derivatives to Aβ Amyloid Fibrils in vitro Specific binding was determined according to the competion binding assay described herein. The determined IC$_{50}$'s in the competion binding assays (using [$^3$H]PIB as radioligand) of compounds of the present invention are shown in Table 1.

TABLE 1

IC$_{50}$'s obtained of exemplified compounds of the present invention when tested in the competion binding assay.

| NAME | IC50 (nM) |
|---|---|
| 2-[6-(methylamino)pyridin-3-yl]-1-benzofuran-5-ol | 46 |
| 5-(5-methoxy-1-benzofuran-2-yl)pyridine-2-carboxamide | 61 |
| 6-(5-hydroxy-1-benzofuran-2-yl)nicotinamide | 43 |
| 5-(5-hydroxy-1-benzofuran-2-yl)pyridine-2-carboxamide | 600 |
| 5-(5-methoxy-1-benzofuran-2-yl)-N-methylpyridin-2-amine | 66 |
| 6-(5-methoxy-1-benzofuran-2-yl)pyridazin-3-amine | 912 |
| 2-(1-benzofuran-2-yl)-6-methoxyimidazo[1,2-a]pyridine | 361 |
| 5-(1-benzothien-2-yl)pyridine-2-carboxamide | 30 |
| 5-(1-benzofuran-2-yl)pyridine-2-carboxamide | 19 |
| 6-(5-methoxy-1-benzofuran-2-yl)nicotinamide | 33 |
| 2-(6-aminopyridazin-3-yl)-1-benzofuran-5-ol | 2705 |
| 2-(6-fluoro-5-methylamino-pyridin-2-yl)-benzofuran-5-ol | 44 |
| 2-(2-fluoro-6-methylamino-pyridin-3-yl)-benzofuran-5-ol | 18 |
| 2-(5-fluoro-6-methylamino-pyridin-3-yl)-benzofuran-5-ol | 32 |

The invention claimed is:

1. A compound or pharmaceutically acceptable salt thereof, wherein:
the compound is:

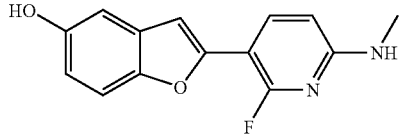

2-(2-fluoro-6-methylamino-pyridiny-3-yl)-benzofuran-5-ol, and
one or more of the atoms of the compound is optionally a detectable isotope.

2. A compound or salt thereof according to claim 1, wherein one or more of the atoms of the compound is a detectable isotope.

3. A compound or salt thereof according to claim 1, wherein:
one to six of the atoms of the compound is the detectable isotope $^3$H,
one to three of the atoms of the compound is the detectable isotope $^{19}$F, or
one of the atoms of the compound is a detectable isotope selected from $^{18}$F and $^{11}$C.

4. A compound or salt thereof according to claim 1, wherein one of the atoms of the compound is the detectable isotope $^{11}$C.

5. A compound or salt thereof according to claim 1, wherein one of the atoms of the compound is the detectable isotope 18F.

6. A pharmaceutical composition for in vivo imaging of amyloid deposits, wherein the composition comprises:
a radio-labeled compound or salt thereof according to claims 1, and
a pharmaceutically acceptable carrier.

* * * * *